United States Patent
Browning et al.

(10) Patent No.: US 6,649,673 B2
(45) Date of Patent: Nov. 18, 2003

(54) SINGLE COMPONENT ROOM TEMPERATURE CURABLE LOW VOC EPOXY COATINGS

(75) Inventors: James Darryl Browning, Columbus, OH (US); Vincent Daniel McGinniss, Sunbury, OH (US); Bhima Rao Vajayendran, Dublin, OH (US)

(73) Assignee: Battelle Memorial Institute, Columbus, OH (US)

( * ) Notice: Subject to any disclaimer, the term of this patent is extended or adjusted under 35 U.S.C. 154(b) by 137 days.

(21) Appl. No.: 09/776,489

(22) Filed: Feb. 2, 2001

(65) Prior Publication Data

US 2003/0008947 A1 Jan. 9, 2003

(51) Int. Cl.$^7$ .............................. C08K 3/34; C08L 63/02
(52) U.S. Cl. ....................... 523/466; 523/454; 523/455; 523/456; 523/462; 528/93; 528/94; 528/118; 528/119
(58) Field of Search ................................. 523/454, 455, 523/456, 462, 466; 528/93, 94, 118, 119

(56) References Cited

U.S. PATENT DOCUMENTS

| | | |
|---|---|---|
| 3,963,680 A | 6/1976 | O'Keefe et al. |
| 4,043,956 A | 8/1977 | Hutton et al. |
| 4,279,793 A | 7/1981 | Wellner et al. |
| 4,299,867 A | 11/1981 | Emmons et al. |
| 4,373,008 A | 2/1983 | Emmons et al. |
| 4,491,538 A | 1/1985 | McCoy |
| 4,533,715 A | 8/1985 | Lee et al. |
| 4,724,253 A | 2/1988 | Cavitt et al. |
| 5,837,785 A | 11/1998 | Kinsho et al. |

FOREIGN PATENT DOCUMENTS

| | | |
|---|---|---|
| DE | 196 28 309 A | 1/1998 |
| DE | 100 26 148 A | 12/2000 |
| EP | 0686 654 A | 12/1995 |
| EP | 0 969 030 A | 1/2000 |
| EP | 0 976 771 | 2/2000 |
| GB | 960236 | 6/1964 |
| GB | 972 988 A | 10/1964 |
| WO | WO 98 50444 A | 11/1998 |

OTHER PUBLICATIONS

Shell Resins, EPON Resin 828, 2/99.
Epoxy Curing Agents and Modifiers; Air Products and Chemicals, Inc., 1998 (2 pgs.).
Seki, K., Amine Epoxy Resin Curing Agent Offers Versatility; Modern Paint and Coatings, Mar. 1995, pp. 36–40.
Meeus, F., New developments in ambient cure epoxy resins for high performance industrialcoatings; JOCCA, 1990, pp. 186–192.
Schneberger, G.L., Using Slovents Effectively; Industrial Paint & Powder, Sep. 1999, pp. 38–42.
Incozol 2, Oxazolidine Moisture Scavenger; Industrial Copolymers Limited, England, (6 pgs.) 1996.
Shell Resins, Heloxy 62 Modifier; Shell Chemical Company (4 pgs.), 1996.
Formulating Acrylate Modified Epoxy/Amine Coatings; Sartomer Application Bulletin, Exton, PA, Feb. 1996, (9 pgs.).
Drake, R., Feature High Performance Adhesives, Structural Adhesives Technology: Two Decades of Enduring Progress; Adhesives Age, Jun. 1998. pp. 26–29.
Double Exposure, Air Products' Advanced Technologies Meet Needs of Changing Marketplace; Adhesives Age, Fe. 1998, p. 34.
Air Products, Ancamine 2280 Curing Agent; Air Products and Chemicals, Inc., 1998, (6 pgs.).
Air Products, Epoxy Curing Agents and Modifiers, Ancamide 2386 Curing Agent; Air Products and Chemicals, Inc., Apr. 1997, pp. 1–9.
Holm, R.T., Ketimines as Latent Epoxy Curing Agents; Journal of Paint Technology, vol. 39, No. 509, Jun. 1967, pp. 385–388.
EPON Curing Agents, Specification and Property Guide; Shell, 1986 (3 pgs.).

*Primary Examiner*—Robert Dawson
*Assistant Examiner*—D. Aylward
(74) *Attorney, Agent, or Firm*—Dinsmore, Shohl LLP

(57) ABSTRACT

A single component epoxy coating precursor and a method for making such a precursor, a low VOC epoxy coating and a method for making such a coating, and a method for making a blocked amine which is more stable than previously known ones.

The single component epoxy coating precursor includes an epoxy resin, a first solvent, and a blocked amine. The single component epoxy coating precursor has a viscosity after 30 days at a temperature of 55° C. of less than 16 stokes.

154 Claims, No Drawings

SINGLE COMPONENT ROOM TEMPERATURE CURABLE LOW VOC EPOXY COATINGS

BACKGROUND OF THE INVENTION

The present invention relates generally to epoxy coatings, and more particularly to the use of blocked amine compounds in making epoxy coatings.

Curable epoxy resin systems are known. Conventional two component epoxy resin systems involve mixing of the epoxy resin and hardener and subsequent application of such mixtures as coatings by various techniques. Once mixed, such systems have short pot lives and must be used within a few hours.

As a result, efforts have been made to develop what are called one component systems. In one component systems, the curing agent is mixed with the epoxy but is inactive. It can be activated at a later time. One type of one component system involves the use of elevated temperature to activate the cross-linking reaction. However, the use of high temperatures is undesirable in many applications.

Another type uses latent cure, blocked amine systems in an attempt to alleviate the problem of reduced shelf life. In blocked amine systems, the amine is reacted with a ketone or aldehyde to form a blocked amine which is mixed with the epoxy resin. The system is activated by the addition of water, typically in the form of ambient moisture. This reverses the blocking reaction, forming the amine and the ketone or aldehyde. The amine then reacts with the uncured epoxy resin, and the ketone or aldehyde either evaporates or co-reacts with the epoxy. In the absence of moisture, such blocked amines systems afford a slight improvement in storage stability over conventional two component systems. However, commercial ketimine-based epoxy resin systems still suffer from limited storage stability, typically having a pot life of less than 24 hours. (Shell, 1986, EPON Curing Agents).

Furthermore, many systems include volatile organic compounds (VOC) or hazardous air pollutants (HAP), which are regulated. Commercial ketimine-based epoxy resin systems have elevated levels of VOCs, generally in excess of 3.5 lbs/gal. Under the current VOC standard for many industrial and maintenance coating applications, the limit is 3.1 lbs/gal of VOCs. This limit is likely to be reduced in the future to less than 2.8 lbs/gal of VOCs.

The use of ketimines as curing agents for epoxy resins is described in R. T. Holm, "Ketimines as Latent Epoxy Curing Agents," J. of Paint Tech., Vol. 39, No. 509, June 1967, pp. 385–388. The VOC levels of these compounds is over 3.5 lbs/gal. The reported viscosity of the formulations containing the various ketimines ranged from about 3 to about 36 stokes after storage for 20 days at 25° C. However, these formulations do not provide the long term stability desired for commercial products. The long term stability of the formulations can be evaluated using accelerated aging testing at 55° C. Two weeks storage at 55° C. is equivalent to a shelf life of about six months, while 30 days storage is equivalent to a shelf life of over 1 year. The shelf life at 55° C. is estimated to be only about 12% of the value at 25° C.

British Patent No. 960,236, which is incorporated herein by reference, attempts to improve the shelf life of ketimine-based single component epoxy coatings by using hydroxyl-containing imines as blocked curing agents. The imines are obtained by reacting one or more imines possessing at least one amino hydrogen and one or more compounds having at least one epoxy group. No shelf life or VOC level is reported for these formulations. U.S. Pat. No. 5,837,785, which is incorporated herein by reference, discloses the use of heterocyclic containing curing agents for use in single component epoxy resin compositions. The heterocycle-containing compound has a backbone chain selected from the group consisting of polyether, polyvinyl, polyester, polyamide, polycarbonate, and novalac chains and at least two heterocyclic groups of the following general formula as side chains:

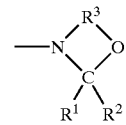

wherein $R^1$ and $R^2$ may be the same or different and each represents hydrogen, straight chain or branched $C_1$ to $C_6$ alkyl or alkenyl, or $C_6$ to $C_8$ aryl; or $R^1$ and $R^2$ taken together with the adjacent carbon atom, represents $C_5$ to $C_7$ cycloalkyl; $R^3$ represents $C_1$ to $C_{10}$ alkylene. A shelf life of 6 months at 40° C. is reported, but no VOC level is given. The viscosity of coating formulations is not disclosed, but it appears to be high for conventional coating applications.

Therefore, there is a need for a single component epoxy coating precursor having improved shelf life and a method for making such a precursor. There is also a need for a low VOC epoxy coating and for a method of making such a coating. There is also a need for a method of making a blocked amine which can be used in a single component epoxy coating precursor.

SUMMARY OF THE INVENTION

The present invention solves this need by providing a single component epoxy coating precursor and a method for making such a precursor, a low VOC epoxy coating and a method for making such a coating, and a method for making a blocked amine which is more stable than previously known ones.

The single component epoxy coating precursor includes an epoxy resin, a first solvent, and a blocked amine. The single component epoxy coating precursor has a viscosity after 30 days at a temperature of 55° C. of less than 16 stokes. It can have a viscosity after 30 days at a temperature of 55° C. of less than 13 stokes, or a viscosity after 30 days at a temperature of 55° C. of less than 7 stokes.

The method for making a single component epoxy coating precursor includes drying an epoxy resin and a blocked amine, combining and mixing the epoxy resin, the blocked amine, and a first solvent to form the single component epoxy coating precursor, wherein the single component epoxy coating precursor has a viscosity after 30 days at a temperature of 55° C. of less than 16 stokes. It can have a viscosity after 30 days at a temperature of 55° C. of less than 13 stokes, or a viscosity after 30 days at a temperature of 55° C. of less than 7 stokes. This level of viscosity stability at 55° C. generally corresponds to over one year of shelf life at room temperature storage conditions.

A reactive diluent optionally can be added to the single component epoxy coating precursor. Reactive diluents include, but are not limited to, modified glycidyl ethers, acrylates, methacrylates, urethane acrylates and combinations thereof. A water scavenger optionally can be added to the single component epoxy coating precursor. Water scavengers include, but are not limited to, molecular sieves, monocyclic bifunctional oxazolidines and combinations thereof. Pigments may be optionally added to the single component epoxy coating precursor. Pigments include, but are not limited to, titanium dioxide, diarylide yellow, iron oxide, raw umber, burnt umber, phthalocyanine blue, cobalt blue, chinese blue, phthalocyanine green, toluidine red, quinacridone red, dicerylide orange, carbon black, furnale black, lampblack, leafing aluminum and non-leaving aluminum.

Other formulating aids such as wetting agents, flow and rheology modifiers, light stability additives, etc., known in the art can be also incorporated.

First solvents which are useful in the present invention include, but are not limited to acetone, p-chlorobenzotrifluoride, t-butyl acetate, methyl isobutyl ketone, methyl propyl ketone and combinations thereof.

Epoxy resins include, but are not limited to, aliphatic epoxy resins, cycloaliphatic epoxy resins, aromatic epoxy resins and combinations thereof.

The single component epoxy coating precursor can have a VOC level of less than about 3 lbs/gal, or a VOC level of less than about 2.8 lbs/gal.

The method of making a low VOC epoxy coating includes drying an epoxy resin and a blocked amine, combining and mixing the epoxy resin, the blocked amine, and a first solvent to form the single component epoxy coating precursor, the single component epoxy coating precursor having a VOC level of less than about 3 lbs/gal, and exposing the single component epoxy coating precursor to water, the single component epoxy coating precursor and water reacting to form the low VOC epoxy coating. The water can be present in any form desired, including, but not limited to liquid water, and moisture in the air. The VOC level can be less than about 2.8 lbs/gal. The single component epoxy coating precursor described above and the blocked amine described below can be used to make the low VOC epoxy coating.

The method for making the blocked amine includes mixing a solvent capable of forming an azeotrope with water, an amine, and an amine blocker selected from ketones and aldehydes in a reaction vessel to form a reaction mixture. Ambient moisture is removed from the reaction vessel. The amine and the amine blocker are reacted to form the blocked amine and water of reaction, and the water of reaction is removed from the reaction mixture while the amine and the amine blocker are reacted. The blocked amine is recovered while maintaining the absence of moisture.

The solvent capable of forming an azeotrope with water includes solvents which can form binary or ternary azeotropes with water. These include, but are not limited to, toluene, xylene and combinations thereof.

The amine can be a polyamine, and it includes but is not limited to, diethylenetriamine, m-xylylenediamine and combinations thereof.

The amine blocker is selected from ketones and aldehydes. The ketones and aldehydes may have a molecular weight in the range of about 30 to about 600. They may have between about 2 and 14 carbon atoms. Suitable ketones include, but are not limited to, methyl isobutyl ketone, methyl ethyl ketone, acetone, phorone, heptanedione, tetramethylheptanedione, adamantone, acetonyl acetone, methylpropylketone and combinations thereof. Suitable aldehydes include, but are not limited to benzaldehyde, salicylaldehyde and combinations thereof.

The yield of blocked amine can be greater than about 90% of the theoretical yield, or greater than about 95% of the theoretical yield, or greater than about 97% of the theoretical yield.

The low VOC epoxy coating includes a reaction product of a single component epoxy coating precursor and water, the single component epoxy coating precursor comprising an epoxy resin and a blocked amine, the single component epoxy coating precursor having a VOC level of less than about 3 lbs/gal. The low VOC epoxy coating can have a VOC level of less than about 2.8 lbs/gal.

DETAILED DESCRIPTION OF THE INVENTION

The blocked amines were prepared according to the following procedure. The chemicals to be used were dried over molecular sieves. A solvent capable of forming an azeotrope with water was placed in a suitably sized round bottom flask fitted with a stir bar, magnetic stir plate, heating mantel, reflux condenser, and a Dean-Stark tube. The solvent capable of forming an azeotrope with water includes, but is not limited to, solvents which can form binary or ternary azeotropes with water. Examples of suitable solvents include, but are not limited to, toluene, xylene and combinations thereof. Toluene was used in these experiments as the solvent capable of forming an azeotrope with water. However, it is to be understood that other solvents capable of forming azeotropes with water could also be used. The flask was charged with an amine, a ketone or aldehyde, and a catalyst. Any appropriate catalyst can be used. Generally, acid based catalysts are used, such as p-toluene sulfonic acid. The neck of the reaction flask was wiped with a small amount of toluene to remove any trace reactants. The flask walls were also rinsed with a small amount of toluene to minimize exposure of the reactants to ambient moisture.

After the reaction mixture was added to the flask, it was purged under a stream of argon for about 5 minutes while stirring to remove ambient moisture and oxygen. The reflux condenser was quickly put in place and fitted with a gas inlet tube to provide a very slight positive pressure. Alternatively, the reflux condenser can be fitted with a drying tube containing Drierite™ to avoid incorporation of atmospheric water during the reaction or the subsequent cooling period before the flask is transferred to a distillation apparatus, such as a Rotovap™. No significant difference was observed in the efficiency of azeotrope or the theoretical mass of water recovered using either arrangement.

Water flow to the condenser was started, and the reaction flask and the Dean-Stark tube were wrapped in foil to improve water azeotroping efficiency. The reaction mixture was then stirred and heated. The mixture was maintained under steady state conditions at about 116° C. while stirring until either 100% of the theoretical water of reaction was recovered or until water ceased to azeotrope. The temperature will depend on the particular solvent used, and it should be about the boiling point of the solvent. Here, with toluene as the solvent (BP about 111° C.), the temperature was about 116° C. Water was drained from the Dean-Stark tube as required to prevent overfilling. The water of reaction recovered was over 90% of the theoretical amount, typically over 95%, and generally in the range of 96% to 99%.

At the end of each run, the reaction flask was cooled overnight to room temperature under a slight increase in initial argon pressure or with the drying tube in place. The positive increase in argon pressure was to prevent the transport of trap oil and moisture into the reaction flask. After cooling to room temperature, the reaction mixture was placed in a Rotovap™ to remove toluene and any unreacted ketone or aldehyde. The bath temperature was 70° C., and the vacuum was increased slowly to about 2 mm Hg over one hour. The reaction flask was returned to ambient pressure under argon, removed from the Rotovap™, and placed in a vacuum oven for two days at 70° C. and about 2 mm Hg to remove any remaining traces of toluene, ketone, or aldehyde. Heat to the vacuum oven was turned off, and the flask was cooled to ambient temperature while maintaining a vacuum. Under a stream of argon, the flask was returned to ambient pressure, placed over mole sieves, and capped. The reaction product was evaluated by infrared analysis for free amine.

Amines made using this procedure were blocked with a variety of different ketones and aldehydes. These blocked amines were then used to make single component epoxy resin precursors. The properties of the precursors and the coatings made from them were then evaluated.

The viscosity of the single component epoxy coating precursors in two solvents, toluene and methylisobutylketone (MIBK), at ambient temperature was monitored. In addition, the viscosity was monitored for the epoxy coating precursors in MIBK at 55° C. The accelerated aging samples were tested on a daily basis for the first 30 days, except on weekends, in order to determine viscosity. The process included removing the samples from the oven, cooling the samples to room temperature, and then measuring the samples in direct comparison with Gardner bubble viscosity tubes. The Gardner bubble viscosity tubes use bubble velocity to determine the viscosity of a sample. The viscosity of the sample is determined by finding the standard tube of known viscosity where the air bubble rises at the same rate with that of the test sample. A viscosity of less than 16 stokes is desirable because formulations remain sprayable with conventional spray equipment at this viscosity.

Coating properties were also evaluated. Draw-down panels were prepared using a #54 wire bound rod over Bonderite iron phosphate treated 3"×6"×0.0032" steel panels and stored at 23° C. and 50% relative humidity to evaluate cure time and the physical properties of the films.

The pencil hardness test is described in Paint Testing Manual by H. A. Gardner and G. G. Sward, 13th Ed. (1972) p. 283–284, which is incorporated herein by reference. The ratings from worst to best are: 6B, 5B, 4B, 3B, 2B, B, HB, F, H, 2H, 3H, 4H, 5H, and 6H.

For the MEK double rubs, a pad made from 10 plies of gauze material is attached to the ball end of a 2 lb ball peen hammer. The pad is saturated with methyl ethyl ketone (MEK) and rubbed across the coated substrate. A constant back and forth motion is used so that only the weight of the hammer applies the force. One double rub is equal to one back and forth movement. The movement is continued until the film is marred and/or begins to be removed by the solvent. One hundred double rubs are required to pass this test.

Other standard tests were also run.

Table 1 shows the formulation of the blocked amine and the epoxy coating precursor, and Tables 2 and 3 show the results of the initial evaluation of the epoxy coating precursors and the epoxy coatings.

The control formulation containing unblocked diethylenetriamine (DETA) cured in 2 hrs as a thin film from MIBK. The bottled control in toluene gelled in 24 hrs, while the control in MIBK gelled in 48 hours under ambient conditions. The control in MIBK stored at 55° C. gelled between 1 and 18 hrs.

In Run 1, an experimental DETA-based curing agent blocked with acetone was used. The experimental DETA-based curing agent was supplied by Shell with the designation S42686, and contained a mixture of DETA, a proprietary amine, and an alkyl phenol amine (hereafter referred to as "experimental DETA"). The film dried to the touch between 0–24 hrs. The toluene and MIBK formulations stored at room temperature gelled in 7 days and 9 days, respectively. The accelerated aging sample gelled within 24 hrs.

In Run 2, the experimental DETA-based curing agent was blocked with MIBK. The drying time for this film was 0–24 hrs. Additional films were prepared from this formulation after 3 weeks of aging at room temperature and after 16 days at 55° C. The films were dry to the touch at 6 hrs and 2 hrs. The films made from the aged formulations were blush-free and showed increased gloss with aging of the bottled formulations. Both samples stored at room temperature remained water like with no change in viscosity. The accelerated aging sample showed no change in viscosity until after 15 days. At that time, the viscosity went from about 0.5 to 4.4 stokes within 24 hrs. The sample remained pourable for 2 more days. Gel time was between 17 and 19 days. A replicate sample gelled in 22–24 days with a similar cure profile.

Run 4 used reagent grade DETA blocked with acetone. The drying time was slow, over 48 hrs, and the accelerated aging sample gelled in less than 24 hrs. These results are similar to the ones with experimental DETA. (Run 2).

DETA (reagent grade) blocked with MIBK was used in Run 5. Two panels were prepared from this formulation, one fresh and the other aged for two days. The drying time for the first panel was 0–24 hrs. The first panel showed a slight blush and a low gloss on cure. The second panel was monitored at 2 hr intervals to more accurately assess drying time. It was dry to the touch in 4 hrs, and showed no blush and excellent gloss (the wet look) after cure. The bottled samples stored at room temperature remained water like for over 8 weeks. The accelerated aging sample gelled after 24 days. A replicate sample also gelled in about 24 days.

In Run 6, lysine [$H_2N(CH_2)_4CH(NH_2)COOH$] was blocked with MIBK. One panel containing a 5% excess of blocked amine based upon 4 primary amines, and another containing a 5% excess based on all reactive hydrogens (typically 5) were prepared. The panels remained tacky after 8 hrs, but were dry to the touch the next morning. Pencil hardness was B at 24 hrs and 1 week. The panels showed poor resistance to MEK. The accelerated aging samples showed no increase in viscosity after 29 days. The sample with the lower concentration of blocked amine gelled in less than 6 months, while the sample with the higher level gelled in less than 5 months.

Run 7 involved the use of DETA blocked with phorone [$(CH_3)C=CHCOCH=C(CH_3)_2$]. Films were dry to the touch in about 8 hrs. The panel containing less blocked amine required 8–10 hrs. Pencil hardness was <B after 24 hrs and 1 week, and solvent resistance was poor. The accelerated aging sample containing the lower level of blocked amine gelled in 25 days. The sample with the higher concentration of blocked amine gelled in 14 days.

In Run 8, DETA blocked with 2-heptanedione [$CH_3(CH2)_4COCH_3$] was used. The films were dry to the touch is 8 hrs. Pencil hardness was B at 24 hrs increasing to F at 1 week. MEK resistance was good, especially for the sample with the higher concentration of blocked amine. The panels were glossy with a slight blush. The mixtures exhibited "crawling" during application. "Crawling" refers to coatings that draw away from the surface and leave holes or voids in the coating. Such bare areas are usually related to the wetting properties of the formulation. The accelerated aging sample with the lower concentration of blocked amine gelled in 25 days, while the sample with the higher concentration gelled at 14 days.

DETA blocked with tetramethyl heptanedione [$(CH_3)_3CCOCH_2COC(CH_3)_3$] was used in Run 9 to evaluate the performance of a diketone. The panels required more than 48 hrs to cure and exhibited inadequate hardness and solvent resistance. The accelerated aging samples showed no change in viscosity after 29 days, and did not gel for more than 6 months.

In Run 10, panels made with DETA blocked with pyruvic aldehyde dimethyl acetyl were tacky, but nearly dry to the touch after 8 hrs, and they were completely dry the next morning. Pencil hardness was B after 24 hours for the lower concentration of the blocked amine, and it was F after 1 week. The panel made from the higher concentration had a pencil hardness that was <B and H for the same time intervals. The solvent resistance was 100 double rubs after 1 week. The panels had a good gloss and light blush. The sample with the higher concentration of blocked amine showed a change in viscosity from 0.5 to 13 strokes after 14 days of accelerated aging, and gelled in 17 days. The sample with the lower concentration gelled after more than 30 days.

Run 11 involved the use of DETA blocked with adamantone. After 8 hours, the panels were dry to the touch. The pencil hardness was H, and the MEK resistance was 100 double rubs after one week. The films were medium amber with a gloss <90 and a slight blush. The viscosity of the formulation with the lower concentration of blocked amine, increased from 0.5 to 4 stokes in 14 days, and it gelled at between 16 and 21 days. The formulation having the higher concentration of blocked amine gelled in 13 days.

In Run 12, DETA blocked with acetonyl acetone [$CH_3COCH_2CH_2COCH_3$] was used. The panels remained soft and too tacky for physical evaluation after one week. After 28 days, no change in viscosity was found in the accelerated aging samples.

Meta-xylylenediamine blocked with MIBK was used in Run 13. Within 8 to 9 hours the panels were dry to the touch. According to the literature, blocked amines prepared from meta-xylylenediamine and MIBK dry to the touch in 4 hours at room temperature in the presence of a phenol accelerator. The pencil hardness for the lower concentration of blocked amine was B after 24 hrs, HB after 48 hrs, and HB after 72 hrs. The MEK double rubs were 50 after 24 hrs, 100 after 48 hrs, and 100 after 72 hrs. The panel passed the direct impact tasting, cross hatch and ¼ inch mandrel bend test. The panel showed good gloss and appearance. The panel containing the higher concentration of blocked amine showed a pencil hardness of F after 24 hrs, F after 48 hrs, and H after 72 hrs. The MEK double rubs results were 90 after 24 hrs, 100 after 48 hrs, and 100 after 72 hrs. This panel also passed the direct impact, cross hatch and ¼ inch mandrel bend tests. No viscosity change occurred until after 30 days of accelerated aging. The formulation with the lower concentration of blocked amine remained unchanged after 40 days of accelerated aging and did not gel for more than 6 months. The formulation having the higher concentration of blocked amine had a viscosity of 2.8 stokes after 40 days, and it did not gel for more than 4.5 months.

Run 14 involved xylylenediamine blocked with diisobutylketone (DIBK). Both panels required more than 48 hrs to dry. They showed a pencil hardness of B after one week. At one week, the MEK double rubs were 20 for the lower concentration and 100 for the higher concentration. The panel passed the other tests. The films were water white with a gloss >90. The aging samples remained unchanged after 13 days.

In summary, Runs 2, 5, 7, 8, 11, and 13 resulted in thin film cure times of 8 hrs or less. Runs 7, 8, and 11 had reasonable viscosity stability at 55° C. The films that produced the best overall physical properties, cure rate, and with over 20 days of viscosity stability at 55° C. were Runs 2, 5, and 13.

From these studies, we found that the effectiveness of the blocking agent in providing long term stability for the single component epoxy coating precursors varies depending on the molecular weight of the blocking agents. A blocking agent having a molecular weight in the range of 30 to 600 provides good long term stability.

The blocked amine used in Run 5, DETA blocked with MIBK, was also evaluated with the addition of titanium dioxide ($TiO_2$). Three formulations of DETA blocked with MIBK were tested under accelerated aging conditions: 3.5 g of DETA blocked with MIBK without $TiO_2$, 3.5 g of DETA blocked with MIBK with 13% $TiO_2$, and 3.8 g of DETA blocked with MIBK with 13% $TiO_2$. The formulations containing $TiO_2$ gelled in 18 days, as compared to 24 days for the sample without $TiO_2$. The 3.5 g of DETA blocked with MIBK with 13% $TiO_2$, was slower to cure than the control. However, by increasing the concentration of the blocked amine (3.8 g of DETA), a slight improvement in thin film cure times and physical properties occurred. Results are further described in Table 4.

Tests were run with reduced solvent (VOC) levels. The results are shown in Table 5 with regard to storage stability, thin film set time and the physical properties of formulations. Similar results occurred for cure and physical properties regardless of the solvent level. The data showed that under accelerated aging conditions, a sample containing half the MIBK concentration gelled in 12 to 14 days, compared to about 24 days for the normal level of MIBK in the control. The control contained 4.0 lbs/gal volatiles while the reduced solvent formulations contained 2.8 lbs/gal of volatiles.

TABLE 1

| | Formulations | | | | | | |
|---|---|---|---|---|---|---|---|
| Run | Control | 1 | 2A | 2B | 2C | 4 | 5A |
| Amine | DETA | DETA-based experimental amine | DETA-based experimental amine | DETA-based experimental amine | DETA-based experimental amine | DETA | DETA |
| Blocking Agent | | Acetone | MIBK | MIBK | MIBK | Acetone | MIBK |
| Draw-down Formulation | | | | | | | |

TABLE 1-continued

| | | | Formulations | | | |
|---|---|---|---|---|---|---|
| Solvent | MIBK | MIBK | MIBK | MIBK | MIBK | MIBK |
| Epoxy resin | | | | | | |
| Blocked Amine | | | | | | |
| Aging | | | None | 3 weeks at RT | 16 days at 55° C. | |

| Run | 5B | 6A | 6B | 7A | 7B | 8A | 8B |
|---|---|---|---|---|---|---|---|
| Amine | DETA | Lysine | Lysine | DETA | DETA | DETA | DETA |
| Blocking Agent | MIBK | MIBK | MIBK | Phorone | Phorone | 2-heptanedione | 2-heptanedione |
| Draw-down Formulation | | | | | | | |
| Solvent | | MIBK - 10 g | MIBK - 10 g | MIBK - 10 g | MIBK - 10 g | MIBK - 10 g | MIBK - 10 g |
| Epoxy resin | | 10 g | 10 g | 10 g | 10 g | 10 g | 10 g |
| Blocked Amine | | 3.55 g | 4.42 g | 3.98 g | 4.96 g | 3.42 g | 4.26 g |
| Aging | | | | | | | |

| Run | 9A | 9B | 10A | 10B | 11A | 11B |
|---|---|---|---|---|---|---|
| Amine | DETA | DETA | DETA | DETA | DETA | DETA |
| Blocking Agent | tetramethyl heptanedione | tetramethyl heptanedione | pyruvic aldehyde dimethyl acetal | pyruvic aldehyde dimethyl accetal | Adamantone | Adamantone |
| Draw-down Formulation | | | | | | |
| Solvent | MIBK - 10 g | MIBK - 10 g | MIBK - 10 g | MIBK - 10 g | MIBK - 10 g | MIBK - 10 g |
| Epoxy resin | 10 g | 10 g | 10 g | 10 g | 10 g | 10 g |
| Blocked Amine | 5.05 g | 6.28 | 3.51 g | 4.38 g | 4.26 g | 5.30 g |
| Aging | | | | | | |

| Run | 12A | 12B | 13A | 13B | 14A | 14B |
|---|---|---|---|---|---|---|
| Amine | DETA | DETA | Xylylenediamine | Xylylenediamine | Xylylenediamine | Xylylenediamine |
| Blocking Agent | Acetonyl acetone | Acetonyl acetone | MIBK | MIBK | DIBK | DIBK |
| Draw-down Formulation | | | | | | |
| Solvent | MIBK - 10 g | MIBK - 10 g | MIBK - 10 g | MIBK - 10 g | MIBK - 10 g | MIBK - 10 g |
| Epoxy resin | 10 g | 10 g | 10 g | 10 g | 10 g | 10 g |
| Blocked Amine | 3.42 g | 4.26 g | 3.5 g | 4.3 g | 4.41 g | 5.49 g |
| Aging | | | | | | |

TABLE 2

Evaluation Blocked Amines

| Run | Time (hrs) | Dry to Touch | Pencil Hardness | MEK Dbl. Rubs | 20 lbs | 40 lbs | Cross Hatch Adhesion | 1/4" Mandrel Bend | Film Color (1 wk) | Gloss (1 wk) | Toluene at RT (Daily/ 24 hrs) | MIBK at RT (Daily/ 24 hrs) | MIBK at 55° C. (Daily/ 24 hrs) |
|---|---|---|---|---|---|---|---|---|---|---|---|---|---|
| Control | | 2 hrs | | | | | | | | | | | |
| | 24 | | 2H | Passed (100) | | | | | Water white blush | | Gelled in 24 hrs | | Gelled in 1–18 hrs |
| | 48 | | 3H | | | | | | | | | Gelled in 48 hrs | |
| | 168-wk | | | Passed (100) | Passed | Passed | Some linear failure; no squares | Very slight stress cracking | | | | | |
| 1 | | 0–24 hrs | | | | | | | | | | | |
| | 24 | | 2H | 51, softening; 24 hr full recovery | | | | | | | | | Gelled in 24 hrs |
| | 48 | | | Passed (100) | | | | | | | | | |
| | 168-wk | | 2H | Passed (100) | Passed | Partial "rim" failure | Passed | Failed; lost adhesion | | | Gelled in 7 days | Gelled in 9 days | |
| 2A | | 0–24 hrs | | | | | | | | | | | |

TABLE 2-continued

Evaluation Blocked Amines

| Run | Time (hrs) | Dry to Touch | Pencil Hardness | MEK Dbl. Rubs | 20 lbs | 40 lbs | Cross Hatch Adhesion | 1/4" Mandrel Bend | Film Color (1 wk) | Gloss (1 wk) | Toluene at RT (Daily/ 24 hrs) | MIBK at RT (Daily/ 24 hrs) | MIBK at 55° C. (Daily/ 24 hrs) |
|---|---|---|---|---|---|---|---|---|---|---|---|---|---|
|  | 24 | Gummy | 2B | 0 |  |  |  |  | Light amber high gloss |  |  |  |  |
|  | 48/72 1 wk | Dry |  H | 0/0 100; softening didn't go to bare metal | Passed | Passed | Passed | Passed |  |  |  |  |  |
|  | 2 wk 3 wk |  | H 2H |  | Passed Passed | Passed Slight "rim" failure | Passed Passed | Passed Passed |  |  |  |  |  |
| 2B | 6 hrs 2 | Sticky |  |  |  |  |  |  | Light amber good gloss |  |  |  |  |
|  | 4 6 | Tacky Dry to touch, FP |  |  |  |  |  |  |  |  |  |  |  |
|  | 8 | Dry to touch, FP, recovers 2 hrs |  |  |  |  |  |  |  |  |  |  |  |
| 2C | 2 | Dry to touch, slight FP |  |  |  |  |  |  | Light amber no blush high gloss (wet look) |  |  |  |  |
|  | 4 | Dry to touch, slight FP |  |  |  |  |  |  |  |  |  |  |  |
|  | 6 | Dry to touch, slight FP |  |  |  |  |  |  |  |  |  |  |  |
|  | 8 | Dry to touch, slight FP, recovers |  |  |  |  |  |  |  |  |  |  | No change after 14 days, Passed aging test Gelled between 17–19 days Replicate gelled in 22–24 days |
|  | 24 |  |  |  |  |  |  |  |  |  |  |  |  |
|  | 48/72 |  | HB | 80 | Passed | Passed | Passed |  |  |  |  |  |  |
|  | 96 1 wk |  | HB F | 90 100 | Passed | Passed | Passed |  |  |  |  |  |  |
| 4 | 24–48 hrs ? |  |  |  |  |  |  |  | Mod amber mod blush orange peel |  |  |  | Water like |
|  | 24 | Tacky | HB | 42 |  |  |  |  |  |  |  |  | Gelled in 24 hrs |
|  | 48/72 | Week-end | HB | 60/75 |  |  |  |  |  |  |  |  |  |
|  | 96 1 wk | Dry | F | 75 100 | Passed | Passed | Slight failure |  |  |  |  |  | No change |

TABLE 2-continued

Evaluation Blocked Amines

| Run | Time (hrs) | Dry to Touch | Pencil Hardness | MEK Dbl. Rubs | 20 lbs | 40 lbs | Cross Hatch Adhesion | 1/4" Mandrel Bend | Film Color (1 wk) | Gloss (1 wk) | Toluene at RT (Daily/ 24 hrs) | MIBK at RT (Daily/ 24 hrs) | MIBK at 55° C. (Daily/ 24 hrs) |
|---|---|---|---|---|---|---|---|---|---|---|---|---|---|
| | 2 wk | | | | | | | | | | | Not monitored Water like | |
| 5A | 0–24 hrs | | | | | | | | | | | | |
| | 24 | | HB | 35 | | | | | Clear low gloss slight blush | | | | |
| | 48/72 | | B/B | 42/65 | | | | | | | | | |
| | 96 | | B | 72 | | | | | | | | | |
| | 1 wk | | B | 90 | | | | | | | | | |
| | 2 wk | | F | 100, slight softening | | | | | | | | | |
| 5B | 4 hrs | | | | | | | | | | | | |
| | 2 | Wet | | | | | | | | | | | |
| | 4 | Dry to touch, slight FP | | | | | | | | | | | |
| | 6 | Dry to touch, slight FP | | | | | | | | | | | |
| | 8 | Dry to touch, no FP | | | | | | | | | | | |
| | 24 | | | | | | | | Clear high gloss no blush | | | | |
| | 1 wk | | | | Passed | Slight "rim" failure | Passed | | | | | | Gelled in about 24 days |
| 6A | 8–24 hrs | | | | | | | | | | | | |
| | 24 | Dry to touch, slight FP | <B | <10 | | | | | | | | | |
| | 1 wk | | B | 15 | Passed | Passed | Passed | Passed | Water white dull slightly bluish | | | | Gelled in less than 5 months |
| 6B | 8–24 hrs | | | | | | | | | | | | |
| | 24/48 72/96 | | B | 20 | | | | | Water white dull slightly bluish | | | | Gelled in less than 6 months |
| | 1 wk | | B | 15 | Passed | Passed | Passed | Passed | | | | | |
| 7A | 8–10 hrs | | | | | | | | | | | | |
| | 24 | | <B | <5 | | | | | | | | | |
| | 1 wk | | <B | 6 | Failed | Failed | Passed | Passed | Dark amber | >90 | | | Gelled in 25 days |
| 7B | 8 hrs | | | | | | | | | | | | |
| | 24 | | <B | <5 | | | | | | | | | |
| | 1 wk | | B | 6 | Failed | Failed | Partial Failure | Passed | Dark amber | >90 | | | Gelled in 14 days |

TABLE 2-continued

Evaluation Blocked Amines

| Run | Time (hrs) | Dry to Touch | Pencil Hardness | MEK Dbl. Rubs | 20 lbs | 40 lbs | Cross Hatch Adhesion | 1/4" Mandrel Bend | Film Color (1 wk) | Gloss (1 wk) | Toluene at RT (Daily/ 24 hrs) | MIBK at RT (Daily/ 24 hrs) | MIBK at 55° C. (Daily/ 24 hrs) |
|---|---|---|---|---|---|---|---|---|---|---|---|---|---|
| 8A | 8 | 7 hrs 7 hrs dry to touch very slight FP | | | | | | | | | | | |
| | 24 | | B | 10 | | | | | | | | | |
| | 1 wk | | F | 100 (dulled film) | Passed | Failed | Passed | Passed | Yellow medium amber blush | <90 | | | Gelled in 14 days |
| 8B | 6 | 6 hrs dry to touch very slight FP | | | | | | | | | | | |
| | 24 | | B | 100 (dulled film) | | | | | | | | | |
| | 1 wk | | F | 100 (no effect) | Passed | Failed | Passed | Failed | Yellow medium amber blush | <90 | | | Gelled in 25 days |
| 9A | 24 | >48 hrs Tacky, FP | | | Gummy | Gummy | | | | | | | |
| | 1 wk | | <B | 10 | Passed | Passed | Passed | Passed | Water white | >90 | | | Gelled in more than 6 months |
| 9B | 24 | >48 hrs Tacky, FP | | | Gummy | Gummy | | | | | | | |
| | 1 wk | | <B | 15 | Passed | Passed | Passed | Passed | | | | | Gelled in more than 6 months |
| 10A | 8 | 8–24 hrs nearly dry | | | | | | | | | | | |
| | | | B | <10 | | | | | | | | | |
| | 1 wk | | F | 100 (dulled film) | Passed | Passed | Passed | Passed | Light amber blush | >90 | | | Gelled in more than 30 days |
| 10B | 8 | 8–24 hrs nearly dry | | | | | | | | | | | |
| | 24 | | <B | 5 | | | | | | | | | |
| | 1 wk | | H | 100 (dulled film) | Passed | Passed | Passed | Failed | Light amber | <90 | | | Gelled in 17 days |
| 11A | | 8–9 hrs | | | | | | | | | | | |
| | 24 | | B | <10 | | | | | | | | | |
| | 1 wk | | H | 100 (dulled film) | Passed | Passed | Passed | Failed | Medium amber blush | <90 | | | Gelled between 16 and 21 days |
| 11B | | 8–9 hrs | | | | | | | | | | | |
| | 24 | | B | 10 | | | | | | | | | |
| | 1 wk | | H | 100 (dulled film) | Passed | Passed | Passed | Failed | Medium amber | <90 | | | Gelled in 13 days |
| 12A | | >1 wk | | | | | | | | | | | |
| 12B | | >1 wk | | | | | | | | | | | |
| 13A | | 9 hrs | | | | | | | | | | | |
| | 24 | | B | 50 | | | | | | | | | |
| | 48 | | HB | 100 | | | | | | | | | |
| | 72 | | HB | 100 | | | | | | | | | |
| | 1 wk | | HB | 100 (dulled film) | Passed | Passed | Passed | Passed | | | | | Gelled in more than 6 mths |

TABLE 2-continued

Evaluation Blocked Amines

| Run | Time (hrs) | Dry to Touch | Pencil Hardness | MEK Dbl. Rubs | 20 lbs | 40 lbs | Cross Hatch Adhesion | 1/4" Mandrel Bend | Film Color (1 wk) | Gloss (1 wk) | Toluene at RT (Daily/ 24 hrs) | MIBK at RT (Daily/ 24 hrs) | MIBK at 55° C. (Daily/ 24 hrs) |
|---|---|---|---|---|---|---|---|---|---|---|---|---|---|
| 13B |  | 8 hrs |  |  |  |  |  |  |  |  |  |  |  |
|  | 24 |  | B | 90 |  |  |  |  |  |  |  |  |  |
|  | 48 |  | HB | 100 |  |  |  |  |  |  |  |  |  |
|  | 72 |  | HB | 100 |  |  |  |  |  |  |  |  |  |
|  | 1 wk |  | HB | 100 (dulled film) | Passed | Passed | Passed | Passed |  |  |  |  | Gelled in more than 4.5 mths |
| 14A |  | >48 hrs |  |  |  |  |  |  |  |  |  |  |  |
|  | 24 |  | Sticky | Sticky |  |  |  |  |  |  |  |  |  |
|  | 1 wk |  | B | 20 | Passed | Passed | Passed | Passed | Water white | >90 |  |  |  |
| 14B |  | >48 hrs |  |  |  |  |  |  |  |  |  |  |  |
|  | 24 |  | Sticky | Sticky |  |  |  |  |  |  |  |  |  |
|  | 1 wk |  | B | 100 (slight dulling) | Passed | Passed | Passed | Passed | Water white | >90 |  |  |  |

TABLE 3

Overall Film Evaluations Based on Visual Observation

| Run | Comments |
|---|---|
| 4 | Moderate blush |
| 6A | Excellent flow upon application, gloss diminished after 8 hrs |
| 6B | Excellent flow upon application, gloss diminished after 8 hrs |
| 7A | Good flow upon application, slight fisheyes |
| 7B | Good flow upon application, slight fisheyes |
| 8A | Poor flow, crawling |
| 8B | Poor flow, crawling |
| 9A | Fairly good flow, slight crawling |
| 10A | Good flow upon application |
| 10B | Good flow upon application |
| 11A | Good flow upon application |
| 11B | Good flow upon application |
| 12A | Poor flow upon application, crawling, fisheyes |
| 12B | Poor flow upon application, crawling, fisheyes |
| 14A | Very good flow upon application |
| 14B | Very good flow upon application |
| 15A | Good flow upon application |
| 15B | Good flow upon application |

TABLE 4

Physical Data for Epoxy Formulations With and Without Titanium Dioxide

| Ingredients | Grams | Hardness (24 hours) FORMULATION (hours) | Dry to touch Day 1 | Day 5 | Day 6 | MEK Double Rubs Day 1 | Day 5 | Day 6 | Gel time (days) | Comments |
|---|---|---|---|---|---|---|---|---|---|---|
| RUN 5 |  |  |  |  |  |  |  |  |  |  |
| 48262-38-16[A] |  |  |  |  |  |  |  |  |  | Passed direct impact, cross hatch and 1/4" mandrel bend testing after 1 week, gloss and appearance excellent |
| 48220-44-09 |  |  |  |  |  |  |  |  |  |  |
| 3.9 VOC |  |  |  |  |  |  |  |  |  |  |
| MIBK-DETA | 3.5 | 5 Hours, NFP | F | H | H | 100 | 100 | 100 | 24 days[A] |  |
| MIBK | 10 |  |  |  |  |  |  |  |  |  |
| EPON 828 | 10 |  |  |  |  |  |  |  |  |  |
| TiO2 | 0 |  |  |  |  |  |  |  |  |  |
| 48262-41-13[B] |  |  |  |  |  |  |  |  |  | Sample very slow to cure after 2 weeks achieved "HB" pencil hardness and 100 MEK double rubs with slight dulling. Passed direct impact, cross hatch and mandrel bend tests. |
| 48220-65-07 |  |  |  |  |  |  |  |  |  |  |
| 3.9 VOC |  |  |  |  |  |  |  |  |  |  |
| MIBK-DETA | 3.5 | 8 hours, sl FP | Too soft | <B | <B | Too soft | 4 | 7 | 18 days[B] |  |

TABLE 4-continued

Physical Data for Epoxy Formulations With and Without Titanium Dioxide

| Ingredients | Grams | FORMULATION Dry to touch (hours) | Hardness (24 hours) Day 1 | Day 5 | Day 6 | MEK Double Rubs Day 1 | Day 5 | Day 6 | Gel time (days) | Comments |
|---|---|---|---|---|---|---|---|---|---|---|
| MIBK | 10 | | | | | | | | | |
| EPON 828 | 10 | | | | | | | | | |
| TiO2 | ~13% | | | | | | | | | |
| 48262-41-28 | | 4 hours, | 2H | | H | 100 | | 100 | 18 days | |
| >4.0 VOC | | DTT, FP | | | | | | | | |
| MIBK-DETA | 3.8 | | | | | | | | | Passed direct impact, cross hatch and 1/4" mandrel bend testing, gloss and appearance excellent |
| MIBK | 10 | | | | | | | | | |
| EPON 828 | 10 | | | | | | | | | |
| TiO2 | ~13% | | | | | | | | | |

$^A$No gel time taken for this sample used gel time for identical formulation 48220-44-09
$^B$No gel time taken for this sample used gel time for identical formulation prepared with dried TiO$_2$ 48220-65-07

TABLE 5

Physical Data for Epoxy Formulations With Different Concentrations of MIBK

| Ingredients | FORMULATION Grams | Dry to touch | Hardness (24 hours) Day 1 | Day 5 | Day 6 | MEK Double Rubs Day 1 | Day 5 | Day 6 | Gel time (days) | Comments |
|---|---|---|---|---|---|---|---|---|---|---|
| Run 2 | | | | | | | | | | |
| 48262-38-07 | | | | | | | | | Gel 17–19 days$^A$ | Passed direct impact, failed 1/4 inch mandrel (rim failure) amber appearance with good gloss (>90) |
| 3.9 VOC | | | | | | | | | Gel 22–24 days$^B$ | |
| MIBKxp-DETA | 3.5 | 6 hours | B | H | H | 40 | 100 | 100 | | |
| MIBK | 10 | DTT. Very slight FP | | | | | | | | |
| EPON 828 | 10 | | | | | | | | | |
| 48262-38-25 | | | | | | | | | NONE | |
| 2.98 VOC | | | | | | | | | | |
| MIBKxp-DETA | 3.5 | 9 hours | <B | F | F | 80 | 100 | 100 | | Passed direct impact, failed 1/4 inch mandrel (rim failure) amber appearance with good gloss (>90) |
| MIBK | 5 | DTT, slight FP | | | | | | | | |
| EPON 828 | 10 | | | | | | | | | |
| Run 5 | | | | | | | | | | |
| 48262-38-16 | | | | | | | | | | |
| 2.98 VOC | | | | | | | | | | |
| MIBK-DETA | 3.5 | 5 Hours, NFP | F | H | H | 100 | 100 | 100 | ~24 days$^C$ | |
| MIBK | 10 | | | | | | | | | |
| EPON 828 | 10 | | | | | | | | | |
| 48262-39-07 | | | | | | | | | | |
| 2.98 VOC | | | | | | | | | | |
| MIBK-DETA | 3.5 | 4 hours | H | 2H | 2H | 100 | 100 | 100 | Gel time 12–14 days$^D$ | Passed direct impact (20 lbs), failed direct impact (40 lbs), passed cross hatch, failed 1/4 inch mandrel bend (2 wks). Amber appearance slight blush, good gloss (<90) |
| MIBK | 5 | | | | | | | | | |
| EPON 828 | 10 | | | | | | | | | |

$^A$Reference sample 48220-28-13 used to determine gel time
$^B$Reference sample 48220-53-07 used to determine gel time
$^C$Reference samples 48262-44-09 and 49-07 used to determine gel time
$^D$Reference samples 48220-65-16 used to determine gel time Another set of tests focused on evaluating reduced VOC formulations. The VOC exempt solvents that were evaluated included acetone and p-chlorobenzotrifluoride (available as Oxsol 100 from Occidental Chemical Corp.). Tertiary butyl acetate (t-butyl acetate), for which exempt status is pending, was also evaluated. The nonexempt solvents included methyl isobutyl ketone (MIBK) and methyl propyl ketone (MPK). The solvents were evaluated in combination with water scavengers, including molecular sieves and Incosol-2® (available from Industrial Copolymers, Ltd.), and several mono and multifunctional reactive diluents. Incosol-2® is a monocyclic bifunctional oxazolidine that reacts with water to form a linear aminoalcohol and an aldehyde.

Eight-five formulations were prepared from xylylenediamine blocked with MIBK. The formulations are shown in Table 6. The materials were dried over mole sieves prior to use. The epoxy resin (EPON 828 available from Miller Stevenson) and the solvent(s) were combined and vortexed for about one minute until the samples were homogenous. Next, the reactive diluent was added, if used. The water scavenger was then added, if used. The samples were vortexed again for about 0.5 to 1.0 minute each, and the blocked amine was added. The samples were vortexed for a third time after which aliquots were transferred to 8 ml glass culture tubes, capped and put in the oven at 55° C. for accelerated aging evaluation. The remaining mixtures were maintained at room temperature for approximately 13 to 14 hours.

The results of the testing of these formulations are shown in Tables 7 and 8.

TABLE 6

Storage Stability Test Matrix Run 20 (MIBK-Xylylenediamine Based System)

| | 742 | | 746 | | 748 | | 757 | | No Reactive Diluent | |
| | | | | | | | | | With Incosol + | With Incosol − 5.0% |
| Reactive Diluent Solvent System | With Incosol | Without Incosol | With Incosol | Without Incosol | With Incosol | Without Incosol | With Incosol | Without Incosol | 2.5% Excess Amine | Excess Amine |
|---|---|---|---|---|---|---|---|---|---|---|
| MIBK | 45C | 5C | 55C | 15C | 65C | 25C | 75C | 35C | 2C | 4C |
| MPK | 47C | 7C | 57C | 17C | 67C | 27C | 77C | 37C | | |
| OXSOL 100 | 49C | 9C | 59C | 19C | 69C | 29C | 79C | 39C | | |
| t-Butyl Acetate | 51C | 11C | 61C | 21C | 71C | 31C | 81C | 41C | | |
| Acetone | 53C | 13C | 63C | 23C | 73C | 33C | 83C | 43C | | |

| | 742/TMPTA | | 746/TMPTA | | 748/TMPTA | | 757/TMPTA | | No Reactive Diluent | |
| | | | | | | | | | With Mole S. + | With Mole S. − 5.0% |
| Reactive Diluent Solvent System | With Mole S | Without Mole S | With Mole S | Without Mole S | With Mole S | Without Mole S | With Mole S | Without Mole S | 2.5% Excess Amine | Excess Amine |
|---|---|---|---|---|---|---|---|---|---|---|
| MIBK | 46C | 6C | 56C | 16C | 66C | 26C | 76C | 36C | 1C | 3C |
| MPK | 48C | 8C | 58C | 18C | 68C | 28C | 78C | 38C | | |
| OXSOL 100 | 50C | 10C | 60C | 20C | 70C | 30C | 80C | 40C | | |
| t-Butyl Acetate | 52C | 12C | 62C | 22C | 72C | 32C | 82C | 42C | | |
| Acetone | 54C | 14C | 64C | 24C | 74C | 34C | 84C | 44C | | |
| MIBK/Oxsol 100 | | | | | | | | | 85C | |

*Ketimine at 2.5% excess unless otherwise indicated

TABLE 7

Storage Stability and Physical Property Data Summary of Reduced VOC Formulations Prepared from MIBK-Xylylenediamine

| Sample ID | Viscosity at 30 Days | VOC | Reactive Diluent | Scavenger | Solvent System | DIT 20 | DIT 40 | Gloss | Drying Time | Hardness (24 H) | Hardness (1 WK) |
|---|---|---|---|---|---|---|---|---|---|---|---|
| 1C | #N/A | 2.68 | None | Mole Sieve + 2.5% Excess Amine | MIBK | Fail | Fail | 72.5 | 10–12 hours | H | 2 H |
| 2C | #N/A | 2.68 | None | Incosol + 2.5% Excess Amine | MIBK | Pass | Fail | 81.2 | 10 hours | H | 2 H |
| 3C | 19 | 2.7 | None | Mole Sieve − 5.0% Excess Amine | MIBK | Pass | Fail | 78 | 10–12 hours | 2 H | 3 H |
| 4C | #N/A | 2.67 | None | Incosol − 5.0% Excess Amine | MIBK | Pass | Fail | 85.5 | 10–12 hours | H | 2 H |
| 5C | 5.5 | 2.69 | 742 | None | MIBK | Pass | Pass | 47.5 | over 10 hours | <B | H |
| 6C | #N/A | 2.69 | 742/TMPTA | None | MIBK | Pass | Fail | 103.5 | over 10 hours | 3 H | 2 H |
| 7C | 3.2 | 2.69 | 742 | None | MPK | Pass | Pass | 52.5 | over 10 hours | <B | 2 H |
| 8C | #N/A | 2.69 | 742/TMPTA | None | MPK | Pass | Fail | 101 | 10–12 hours | 2 H | 2 H |
| 9C | #N/A | 1.33 | 742 | None | OXSOL 100 | Pass | Very Slight Fail | 61.7 | over 10 hours | <B | B |

TABLE 7-continued

Storage Stability and Physical Property Data Summary of Reduced VOC Formulations Prepared from MIBK-Xylylenediamine

| Sample ID | Viscosity at 30 Days | VOC | Reactive Diluent | Scavenger | Solvent System | DIT 20 | DIT 40 | Gloss | Drying Time | Hardness (24 H) | Hardness (1 WK) |
|---|---|---|---|---|---|---|---|---|---|---|---|
| 10C | #N/A | 1.47 | 742/TMPTA | None | OXSOL 100 | Fail | Fail | 100.2 | over 10 hours | 3 H | 2 H |
| 11C | #N/A | 1.48 | 742 | None | t-Butyl Acetate | Pass | Pass | 64.2 | over 10 hours | <B | H |
| 12C | #N/A | 1.61 | 742/TMPTA | None | t-Butyl Acetate | Pass | Fail | 100 | over 10 hours | 2 H | 2 H |
| 13C | 0.85 | 1.53 | 742 | None | Acetone | Pass | Slight Failure | 45.1 | over 10 hours | H | 2 H |
| 14C | #N/A | 1.67 | 742/TMPTA | None | Acetone | Pass | Fail | 102.5 | 10–12 hours | 3 H | 4 H |
| 15C | 2.8 | 2.69 | 746 | None | MIBK | Pass | Pass | 38.3 | over 10 hours | <B | 2 H |
| 16C | #N/A | 2.7 | 746/TMPTA | None | MIBK | Fail | Fail | 89.5 | over 10 hours | 2 H | 2 H |
| 17C | 2.5 | 2.69 | 746 | None | MPK | Pass | Pass | 34.9 | over 10 hours | <B | F |
| 18C | #N/A | 2.7 | 746/TMPTA | None | MPK | Pass | Fail | 80.4 | over 10 hours | 3 H | 2 H |
| 19C | #N/A | 1.3 | 746 | None | OXSOL 100 | Pass | Pass | 48.2 | over 10 hours | <B | F |
| 20C | #N/A | 1.43 | 746/TMPTA | None | OXSOL 100 | Pass | Fail | 97.4 | over 10 hours | 2 H | 4 H |
| 21C | 6.8 | 1.44 | 746 | None | t-Butyl Acetate | Pass | Pass | 45.4 | over 10 hours | <B | 2 H |
| 22C | #N/A | 1.58 | 746/TMPTA | None | t-Butyl Acetate | Pass | Fail | 95.4 | over 10 hours | 2 H | 3 H |
| 23C | 2.25 | 1.49 | 746 | None | Acetone | Pass | Pass | 25.5 | over 10 hours | <B | F |
| 24C | #N/A | 1.63 | 746/TMPTA | None | Acetone | Pass | Fail | 97.1 | over 10 hours | 2 H | 2 H |
| 25C | 1.65 | 2.7 | 748 | None | MIBK | Pass | Pass | 17.6 | over 10 hours | <B | F |
| 26C | #N/A | 2.69 | 748/TMPTA | None | MIBK | Pass | Fail | 96.7 | over 10 hours | H | 2 H |
| 27C | 2 | 2.7 | 748 | None | MPK | Pass | Pass | 31 | over 10 hours | <B | HB |
| 28C | #N/A | 2.69 | 748/TMPTA | None | MPK | Pass | Fail | 82.7 | over 10 hours | 2 H | 2 H |
| 29C | 13 | 1.22 | 748 | None | OXSOL 100 | Pass | Pass | 29.1 | over 10 hours | <B | HB |
| 30C | #N/A | 1.42 | 748/TMPTA | None | OXSOL 100 | Pass | Fail | 90 | over 10 hours | 2 H | 2 H |
| 31C | 5.5 | 1.37 | 748 | None | t-Butyl Acetate | Pass | Pass | 17.3 | over 10 hours | <B | <B |
| 32C | #N/A | 1.56 | 748/TMPTA | None | t-Butyl Acetate | Pass | Pass | 93 | over 10 hours | 2 H | 2 H |
| 33C | 1.4 | 1.42 | 748 | None | Acetone | Pass | Pass | 33.2 | over 10 hours | <B | F |
| 34C | #N/A | 1.62 | 748/TMPTA | None | Acetone | Pass | Pass | 98 | over 10 hours | 2 H | 4 H |
| 35C | #N/A | 2.69 | 757 | None | MIBK | Pass | Fail | 60.5 | 10–12 hours | 2 H | 2 H |
| 36C | #N/A | 2.68 | 757/TMPTA | None | MIBK | Pass | Fail | 99.4 | over 10 hours | 2 H | 4 H |
| 37C | 13 | 2.69 | 757 | None | MPK | Pass | Slight Failure | 52.6 | over 10 hours | 2 H | 2 H |
| 38C | #N/A | 2.68 | 757/TMPTA | None | MPK | Pass | Fail | 99.1 | 10–12 hours | 2 H | 4 H |
| 39C | #N/A | 1.38 | 757 | None | OXSOL 100 | Pass | Slight Failure | 72 | 10–12 hours | H | 2 H |
| 40C | #N/A | 1.48 | 757/TMPTA | None | OXSOL 100 | Pass | Pass | 99.6 | over 10 hours | 3 H | 4 H |
| 41C | #N/A | 1.53 | 757 | None | t-Butyl Acetate | Pass | Very Slight Fail | 63.3 | over 10 hours | F | 2 H |
| 42C | #N/A | 1.62 | 757/TMPTA | None | t-Butyl Acetate | Pass | Fail | 99.4 | over 10 hours | 2 H | 2 H |
| 43C | 4.4 | 1.58 | 757 | None | Acetone | Pass | Slight Failure | 60.8 | 10–12 hours | H | H |
| 44C | #N/A | 1.68 | 757/TMPTA | None | Acetone | Pass | Fail | 101.9 | over 10 hours | 4 H | 4 H |

TABLE 7-continued

Storage Stability and Physical Property Data Summary of Reduced VOC Formulations Prepared from MIBK-Xylylenediamine

| Sample ID | Viscosity at 30 Days | VOC | Reactive Diluent | Scavenger | Solvent System | DIT 20 | DIT 40 | Gloss | Drying Time | Hardness (24 H) | Hardness (1 WK) |
|---|---|---|---|---|---|---|---|---|---|---|---|
| 45C | 5.5 | 2.69 | 742 | Incosol | MIBK | Pass | Pass | 35 | 10–24 hours | <B | B |
| 46C | N/A | 2.69 | 742/TMPTA | Mole Sieve | MIBK | Pass | Fail | 101.3 | 10–24 hours | 2 H | 4 H |
| 47C | 3.2 | 2.69 | 742 | Incosol | MPK | Pass | Pass | 29.6 | 10–24 hours | <B | <B |
| 48C | #N/A | 2.69 | 742/TMPTA | Mole Sieve | MPK | Pass | Fail | 98.5 | 10–24 hours | H | 2 H |
| 49C | #N/A | 1.32 | 742 | Incosol | OXSOL 100 | Pass | Pass | 54.5 | 10–24 hours | <B | HB |
| 50C | #N/A | 1.47 | 742/TMPTA | Mole Sieve | OXSOL 100 | Pass | Fail | 95.4 | 10–24 hours | 2 H | 2 H |
| 51C | 13 | 1.46 | 742 | Incosol | t-Butyl Acetate | Pass | Pass | 54.5 | 10–24 hours | HB | HB |
| 52C | #N/A | 1.61 | 742/TMPTA | Mole Sieve | t-Butyl Acetate | Pass | Fail | 88.4 | 10–24 hours | 2 H | 2 H |
| 53C | 0.85 | 1.52 | 742 | Incosol | Acetone | Pass | Very Slight Fail | 42.5 | 10–24 hours | <B | F |
| 54C | 2.8 | 1.67 | 742/TMPTA | Mole Sieve | Acetone | Pass | Fail | 101.2 | 10–24 hours | 2 H | 4 H |
| 55C | 2.5 | 2.69 | 746 | Incosol | MIBK | Pass | Pass | 32.3 | 10–24 hours | <B | HB |
| 56C | #N/A | 2.7 | 746/TMPTA | Mole Sieve | MIBK | Pass | Slight Failure | 84 | 10–24 hours | 2 H | 2 H |
| 57C | 1.65 | 2.69 | 746 | Incosol | MPK | Pass | Pass | 21 | 10–24 hours | <B | B |
| 58C | 13 | 2.7 | 746/TMPTA | Mole Sieve | MPK | Pass | Pass | 94.5 | 10–24 hours | 2 H | 4 H |
| 59C | #N/A | 1.29 | 746 | Incosol | OXSOL 100 | Pass | Pass | 45.6 | 10–24 hours | <B | H |
| 60C | #N/A | 1.43 | 746/TMPTA | Mole Sieve | OXSOL 100 | Pass | Fail | 92.3 | 10–24 hours | H | 4 H |
| 61C | 5.5 | 1.43 | 746 | Incosol | t-Butyl Acetate | Pass | Fail | 38.5 | 10–24 hours | F | H |
| 62C | #N/A | 1.58 | 746/TMPTA | Mole Sieve | t-Butyl Acetate | Pass | Fail | 93.2 | 10–24 hours | 3 H | 3 H |
| 63C | 1.25 | 1.48 | 746 | Incosol | Acetone | Pass | Pass | 24.4 | 10–24 hours | F | F |
| 64C | 3.7 | 1.63 | 746/TMPTA | Mole Sieve | Acetone | Pass | Slight Failure | 99.2 | 10–24 hours | 2 H | 4 H |
| 65C | 2.25 | 2.7 | 748 | Incosol | MIBK | Pass | Pass | 16.9 | 10–24 hours | H | B |
| 66C | N/A | 2.69 | 748/TMPTA | Mole Sieve | MIBK | Pass | Pass | 94 | 10–24 hours | H | 4 H |
| 67C | 1.4 | 2.7 | 748 | Incosol | MPK | Pass | Pass | 15.3 | 10–24 hours | <B | B |
| 68C | 13 | 2.69 | 748/TMPTA | Mole Sieve | MPK | Pass | Pass | 96.2 | 10–24 hours | H | 2 H |
| 69C | #N/A | 1.21 | 748 | Incosol | OXSOL 100 | Pass | Pass | 21.6 | 10–24 hours | <B | B |
| 70C | #N/A | 1.42 | 748/TMPTA | Mole Sieve | OXSOL 100 | Pass | Fail | 91.2 | 10–24 hours | 2 H | 3 H |
| 71C | 4.7 | 1.36 | 748 | Incosol | t-Butyl Acetate | Pass | Pass | 22.8 | 10–24 hours | <B | F |
| 72C | #N/A | 1.46 | 748/TMPTA | Mole Sieve | t-Butyl Acetate | Pass | Pass | 83.6 | 10–24 hours | H | 2 H |
| 73C | 0.65 | 1.41 | 748 | Incosol | Acetone | Pass | Pass | 36.9 | 10–24 hours | <B | <B |
| 74C | 3.7 | 1.62 | 748/TMPTA | Mole Sieve | Acetone | Pass | Pass | 91 | 10–24 hours | H | 4 H |
| 75C | #N/A | 2.69 | 757 | Incosol | MIBK | Pass | Slight Failure | 50.7 | 10–24 hours | 2 H | 2 H |
| 76C | #N/A | 2.68 | 757/TMPTA | Mole Sieve | MIBK | Pass | Fail | 92.1 | 10–24 hours | 2 H | 4 H |
| 77C | 9 | 2.69 | 757 | Incosol | MPK | Pass | Slight Failure | 45.5 | 10–24 hours | F | F |
| 78C | #N/A | 2.68 | 757/TMPTA | Mole Sieve | MPK | Pass | Pass | 96.8 | 10–24 hours | 2 H | 4 H |
| 79C | #N/A | 1.37 | 757 | Incosol | OXSOL 100 | Pass | Pass | 65 | 10–24 hours | H | 2 H |

TABLE 7-continued

Storage Stability and Physical Property Data Summary of Reduced VOC Formulations Prepared from MIBK-Xylylenediamine

| Sample ID | Viscosity at 30 Days | VOC | Reactive Diluent | Scavenger | Solvent System | DIT 20 | DIT 40 | Gloss | Drying Time | Hardness (24 H) | Hardness (1 WK) |
|---|---|---|---|---|---|---|---|---|---|---|---|
| 80C | #N/A | 1.48 | 757/TMPTA | Mole Sieve | OXSOL 100 | Pass | Pass | 94.9 | 10–24 hours | 2 H | 4 H |
| 81C | #N/A | 1.51 | 757 | Incosol | t-Butyl Acetate | Pass | Pass | 62.7 | 10–24 hours | <B | 2 H |
| 82C | #N/A | 1.62 | 757/TMPTA | Mole Sieve | t-Butyl Acetate | Pass | Pass | 93.7 | 10–24 hours | 2 H | >4 H |
| 83C | 2.5 | 1.68 | 757 | Incosol | Acetone | Pass | Slight Failure | 49.6 | 10–24 hours | F | F |
| 84C | 5.5 | 1.63 | 757/TMPTA | Mole Sieve | Acetone | Pass | Pass | 95.1 | 10–24 hours | H | 4 H |
| 85C | 0.5 | 3.05 | None | Mole Sieve | MIBK/ OXSOL 100 | Pass | Very Slight Fail | 76.5 | 10–24 hours | H | 2 H |

TABLE 8

Overall Film Evaluations Based on Visual Observations

| Sample ID | Comments |
|---|---|
| 1C | Irregular flow pattern & lower gloss indicate some incompatibility |
| 2C | Irregular flow pattern & high low gloss indicate some incompatibility |
| 3C | Fairly good flow and gloss but brittle film |
| 4C | Good gloss and flow but brittle film |
| 5C | Good flow but "high-low" gloss pattern indicates incompatibility |
| 6C | Excellent gloss, good flow but brittle film |
| 7C | Good flow but "high-low" gloss pattern indicates incompatibility |
| 8C | Excellent flow & gloss but brittle film |
| 9C | Good flow but "high-low" glass pattern indicates incompatibility |
| 10C | Excellent gloss, good flow but very brittle film |
| 11C | Good flow but "high-low" gloss pattern indicates incompatibility |
| 12C | Excellent gloss & flow but brittle film |
| 13C | Classic example of "high low" gloss pattern & incompatibility |
| 14C | Excellent gloss & flow but brittle film |
| 15C | Good flow but poor gloss |
| 16C | Good gloss, excellent flow but brittle film |
| 17C | Good flow, poor gloss, good flexibility |
| 18C | Good flow & gloss but slight haze; brittle film |
| 19C | Excellent flow but poor gloss; flexible film |
| 20C | Excellent gloss & flow but brittle film |
| 21C | Excellent flow but poor gloss; flexible film |
| 22C | Excellent flow & good but brittle film |
| 23C | Good flow, poor gloss but brittle film |
| 24C | Outstanding gloss & flow but brittle film |
| 25C | Poor gloss & flow; blush |
| 26C | Excellent gloss, moderate flow; brittle film |
| 27C | Low gloss, moderately good flow; blush; flexible film |
| 28C | Fairly good flow but irregular gloss indicates incompatibility |
| 29C | Poor gloss; blush, but good flexible film |
| 30C | Excellent gloss; irregular flow; brittle film |
| 31C | Very poor gloss; film soft, mars easily |
| 32C | Excellent gloss; erratic flow pattern; flexible film |
| 33C | Poor flow pattern, low gloss due to incompatibility |
| 34C | Outstanding gloss, flow hardness & flexibility (*) |
| 35C | Classic "hi h-low" loss attern of incompatibility |
| 36C | Outstanding gloss, erratic flow pattern; brittle film |
| 37C | "high-low" gloss, erratic flow reflects incompatibility |
| 38C | Good gloss & flow but brittle film |
| 39C | "High-low" gloss, erratic flow reflects incompatibility |
| 40C | Excellent gloss, slightly erratic flow, but good flexibility |
| 41C | High-low gloss, erratic flow; incompatibility, flexible film |
| 42C | Outstanding gloss & flow; brittle film |
| 43C | "High-low" gloss; erratic flow reflect incompatibility |
| 44C | Outstanding gloss, good-flow but brittle film |
| 45C | Poor gloss, "high-low" gloss; incompatible but flexible |
| 46C | Outstanding gloss, good flow but brittle film |
| 47C | Poor gloss ("high-low" ) reflect incompatibility flexible film |
| 48C | Outstanding gloss, very good flow but brittle film |
| 49C | Good flow pattern & flexibility but poor gloss |
| 50C | Very good gloss & flow but brittle film |
| 51C | Good flow & flexibility but poor gloss |
| 52C | Good gloss; fairly good flow but brittle film |
| 53C | Classic "high-low" gloss pattern; incompatible flexible film |
| 54C | Outstanding gloss; very good flow but brittle film |
| 55C | Poor flow and gloss; incompatible but flexible film |
| 56C | Very good gloss, flow and relatively good flexibility |
| 57C | Poor flow & gloss; incompatible but flexible film |
| 58C | Outstanding gloss, flow, hardness & flexibility* |
| 59C | Poor flow & gloss; blush, but flexible film |
| 60C | Good gloss & flow but brittle film |
| 61C | Good flow but poor gloss flexible film |
| 62C | Good gloss & glow but brittle film |
| 63C | Poor gloss & flow; incompatible but flexible films |
| 64C | Excellent gloss & flow but brittle film |
| 65C | Poor gloss and flow; soft film; mars easily; blush |
| 66C | Very good gloss, flow & flexibility |
| 67C | Poor gloss; good flow & flexible film |
| 68C | Very good gloss, flow, hardness & flexibility* |
| 69C | Poor gloss; film soft; mars easily, flexible film |
| 70C | Good gloss & flow but brittle film |
| 71C | Poor gloss; film soft, mars easily but flexible |
| 72C | Gloss & flexibility good but "mottled" flow is a problem |
| 73C | Poor gloss, poor flow film soft & mars easily |
| 74C | Very good gloss, flow, hardness & flexibility* |
| 75C | "High-low" gloss pattern reflects incompatibility |
| 76C | Excellent gloss slightly erratic flow & brittle film |
| 77C | Classic "high-low" gloss incompatibility |
| 78C | Very good gloss, flow, hardness & flexibility* |
| 79C | Nice looking film but poor gloss; film flexible |
| 80C | Very good gloss, flow, hardness & flexibility* |
| 81C | Nice looking film but poor gloss, film flexible |
| 82C | Good gloss & flow, hardness & flexibility |
| 83C | "High-low" gloss pattern reflects incompatibility |

TABLE 8-continued

Overall Film Evaluations Based on Visual Observations

| Sample ID | Comments |
|---|---|
| 84C | Very good gloss, flow, hardness & flexibility* |
| 85C | Nice looking film but haze hinders gloss flexible. |

Note: Incompatibility in the strictest sense refers to the fact that a portion of the film appears to be insoluble in the residual solvent or reactive diluents.
*Superior film in all aspects except (slightly reduced) gloss.

After 30 days of accelerated aging, thirty-five of the eighty-five formulation evaluated had measured viscosities of 16 stokes or less, as shown in Table 9. The VOC level of these formulations ranged from 1.22 to 3.05 lbs/gal.

Of those 35 formulations, 29 had viscosities of 7 stokes or less, as shown in Table 10. The VOC level for these formulations ranged from 1.36 to 3.05 lbs/gal.

Of the 29 formulations with viscosities of 7 stokes or less, 12 contained Incosol-2® as a water scavenger, 12 contained no water scavenger, and five contained mole sieves. Only the mole sieves were tested in combination with the reactive diluent trimethylolpropanetriacrylate (TMPTA). The formulations containing TMPTA gelled faster than formulations without TMPTA, regardless of the solvent. In addition, six of the 20 TMPTA/mole sieve formulations remained sprayable after thirty days of accelerated aging. None of the samples containing TMPTA without mole sieves maintained acceptable viscosities after thirty days of accelerated aging.

Five formulations had a viscosity of 1.25 stokes or less and remained water-like. The VOC level for these formulations ranged from 1.41 to 3.05 lbs/gal. Samples 13C, 53C, 63C, and 73C contained acetone as a solvent and sample 85C contained equal parts of acetone and p-chlorobenzotrifluoride as a solvent. None of the five samples contained a multifunctional reactive diluent. Thin films made from these formulations were characterized by low gloss and inadequate hardness.

Draw-down panels were prepared with a #54 wire bound rod over Bonderite 1000 iron phosphate treated steel panels that were 3"×6"×0.0032". The panels were held at a constant temperature of 75° F./50 RH and then observed at two-hour increments for ten hours to determine drying time. The majority of the panels required 10–12 hours or more before they were dry to the touch. The samples evaluated in the first phase using the same ketimine dried in 8–10 hours. The slower drying time is attributable to three factors. First, formulations in the second phase had a 2.5 wt % excess amine instead of 5 wt % as used in the first phase experiments. Second, the average coating thickness was 1.83 mils, due to the higher percent solids associated with the panel, rather than about 0.8 mils as in the previous panels. Finally, the constant temperature room was 73° F./45% RH during the thin film dry period, whereas, the previous panels were maintained in a constant temperature room at 75° F./50% RH. These conditions are slightly less favorable and would slightly retard cure time.

Comparing the effects of the reactive diluents on the coatings, the panels containing TMPTA as a reactive diluent had better hardness and gloss. Among the Epodil™ reactive modifiers, Epodil™ 757, a bifunctional epoxy resin, also exhibited good gloss and hardness. Since the other reactive diluents are monofunctional, these results are consistent with conventional coating chemistry. In summary, independent of VOC levels and storage stability, many test panels show excellent hardness and gloss while still maintaining sufficient flexibility to pass the impact testing.

Four formulations remained sprayable after 30 days of accelerated aging at 55° C. regardless of base solvent, had gloss values of greater than or equal to 85, passed both 20/40 pound impact testing, and had a pencil hardness of greater than or equal to H after 1 week. The four formulations that met the above criteria are 58C, 68C, 74C, and 84C. Two of these contain MPK as a solvent (Samples 58C and 68C), and two contain acetone (Samples 74C and 84C). The viscosity of both MPK formulations was 13 stokes at day 30, which puts the viscosities around the middle of the acceptable range. As a result, these formulations should remain easily sprayable for months, have acceptable VOC levels (2.7 and 2.69 lbs/gal, respectively), and good physical properties. Samples 74C and 84C have very low VOC levels (1.62 and 1.63 lbs/gal, respectively) and retained near water-like viscosities after accelerated aging for 30 days.

Many of the samples maintained acceptable viscosities for about six months or more, based on accelerated aging projection, with acceptable physicals and VOC levels.

TABLE 9

Formulations With Viscosities ≦16 Stokes After 30 Days of Accelerated Aging At 55° C.

| Sample ID | Viscosity at 30 Days | VOC | Reactive Diluent | Scavenger | Solvent System | DIT 20 | Gloss | Hardness (1 WK) |
|---|---|---|---|---|---|---|---|---|
| 5C | 5.5 | 2.69 | 742 | None | MIBK | Pass | 47.5 | H |
| 7C | 3.2 | 2.69 | 742 | None | MPK | Pass | 52.5 | 2 H |
| 13C | 0.85 | 1.53 | 742 | None | Acetone | Pass | 45.1 | 2 H |
| 15C | 2.8 | 2.69 | 746 | None | MIBK | Pass | 38.3 | 2 H |
| 17C | 2.5 | 2.69 | 746 | None | MPK | Pass | 34.9 | F |
| 21C | 6.8 | 1.44 | 746 | None | t-Butyl Acetate | Pass | 45.4 | 2 H |
| 23C | 2.25 | 1.49 | 746 | None | Acetone | Pass | 25.5 | F |
| 25C | 1.65 | 2.7 | 748 | None | MIBK | Pass | 17.6 | F |
| 27C | 2 | 2.7 | 748 | None | MPK | Pass | 31 | HB |
| 29C | 13 | 1.22 | 748 | None | OXSOL 100 | Pass | 29.1 | HB |
| 31C | 5.5 | 1.37 | 748 | None | t-Butyl Acetate | Pass | 17.3 | <B |

TABLE 9-continued

Formulations With Viscosities ≤16 Stokes After 30 Days of Accelerated Aging At 55° C.

| Sample ID | Viscosity at 30 Days | VOC | Reactive Diluent | Scavenger | Solvent System | DIT 20 | Gloss | Hardness (1 WK) |
|---|---|---|---|---|---|---|---|---|
| 33C | 1.4 | 1.42 | 748 | None | Acetone | Pass | 33.2 | F |
| 37C | 13 | 2.69 | 757 | None | MPK | Pass | 52.6 | 2 H |
| 43C | 4.4 | 1.58 | 757 | None | Acetone | Pass | 60.8 | H |
| 45C | 5.5 | 2.69 | 742 | Incosol | MIBK | Pass | 35 | B |
| 47C | 3.2 | 2.69 | 742 | Incosol | MPK | Pass | 29.6 | <B |
| 51C | 13 | 1.46 | 742 | Incosol | t-Butyl Acetate | Pass | 54.5 | HB |
| 53C | 0.85 | 1.52 | 742 | Incosol | Acetone | Pass | 42.5 | F |
| 54C | 2.8 | 1.67 | 742/TMPTA | Mole Sieve | Acetone | Pass | 101.2 | 4 H |
| 55C | 2.5 | 2.69 | 746 | Incosol | MIBK | Pass | 32.3 | HB |
| 57C | 1.65 | 2.69 | 746 | Incosol | MPK | Pass | 21 | B |
| 58C | 13 | 2.7 | 746/TMPTA | Mole Sieve | MPK | Pass | 94.5 | 4 H |
| 61C | 5.5 | 1.43 | 746 | Incosol | t-Butyl Acetate | Pass | 38.5 | H |
| 63C | 1.25 | 1.48 | 746 | Incosol | Acetone | Pass | 24.4 | F |
| 64C | 3.7 | 1.63 | 746/TMPTA | Mole Sieve | Acetone | Pass | 99.2 | 4 H |
| 65C | 2.25 | 2.7 | 748 | Incosol | MIBK | Pass | 16.9 | B |
| 67C | 1.4 | 2.7 | 748 | Incosol | MPK | Pass | 15.3 | B |
| 68C | 13 | 2.69 | 748/TMPTA | Mole Sieve | MPK | Pass | 96.2 | 2 H |
| 71C | 4.7 | 1.36 | 748 | Incosol | t-Butyl Acetate | Pass | 22.8 | F |
| 73C | 0.65 | 1.41 | 748 | Incosol | Acetone | Pass | 36.9 | <B |
| 74C | 3.7 | 1.62 | 748/TMPTA | Mole Sieve | Acetone | Pass | 91 | 4 H |
| 77C | 9 | 2.69 | 757 | Incosol | MPK | Pass | 45.5 | F |
| 83C | 2.5 | 1.68 | 757 | Incosol | Acetone | Pass | 49.6 | F |
| 84C | 5.5 | 1.63 | 757/TMPTA | Mole Sieve | Acetone | Pass | 95.1 | 4 H |
| 85C | 0.5 | 3.05 | None | Mole Sieve | MIBK/Oxsol 100 | Pass | 76.5 | 2 H |

TABLE 10

Formulations With Viscosities ≤7 Stokes After 30 Days of Accelerated Aging At 55° C.

| Sample ID | Viscosity @ 30 Days | VOC | Reactive Diluent | Scavenger | Solvent System | DIT 20 | DIT 40 | Gloss | Hardness (24 H) | Hardness (1 WK) |
|---|---|---|---|---|---|---|---|---|---|---|
| 5C | 5.5 | 2.69 | 742 | None | MIBK | Pass | Pass | 47.5 | <B | H |
| 7C | 3.2 | 2.69 | 742 | None | MPK | Pass | Pass | 52.5 | <B | 2 H |
| 13C | 0.85 | 1.53 | 742 | None | Acetone | Pass | Slight Failure | 45.1 | H | 2 H |
| 15C | 2.8 | 2.69 | 746 | None | MIBK | Pass | Pass | 38.3 | <B | 2 H |
| 17C | 2.5 | 2.69 | 746 | None | MPK | Pass | Pass | 34.9 | <B | F |
| 21C | 6.8 | 1.44 | 746 | None | t-Butyl Acetate | Pass | Pass | 45.4 | <B | 2 H |
| 23C | 2.25 | 1.49 | 746 | None | Acetone | Pass | Pass | 25.5 | <B | F |
| 25C | 1.65 | 2.7 | 748 | None | MIBK | Pass | Pass | 17.6 | <B | F |
| 27C | 2 | 2.7 | 748 | None | MPK | Pass | Pass | 31 | <B | HB |
| 31C | 5.5 | 1.37 | 748 | None | t-Butyl Acetate | Pass | Pass | 17.3 | <B | <B |
| 33C | 1.4 | 1.42 | 748 | None | Acetone | Pass | Pass | 33.2 | <B | F |
| 43C | 4.4 | 1.58 | 757 | None | Acetone | Pass | Slight Failure | 60.8 | H | H |
| 45C | 5.5 | 2.69 | 742 | Incosol | MIBK | Pass | Pass | 35 | <B | B |
| 47C | 3.2 | 2.69 | 742 | Incosol | MPK | Pass | Pass Slight Fail | 29.6 | <B | <B |
| 53C | 0.85 | 1.52 | 742 | Incosol | Acetone | Pass | Very Slight Fail | 42.5 | <B | F |
| 54C | 2.8 | 1.67 | 742/TMPTA | Mole Sieve | Acetone | Pass | Fail | 101.2 | 2 H | 4 H |
| 55C | 2.5 | 2.69 | 746 | Incosol | MIBK | Pass | Pass | 32.3 | <B | HB |
| 57C | 1.65 | 2.69 | 746 | Incosol | MPK | Pass | Pass | 21 | <B | B |
| 61C | 5.5 | 1.43 | 746 | Incosol | t-Butyl Acetate | Pass | Fail | 38.5 | F | H |
| 63C | 1.25 | 1.48 | 746 | Incosol | Acetone | Pass | Pass | 24.4 | F | F |

TABLE 10-continued

Formulations With Viscosities ≦7 Stokes After 30 Days of Accelerated Aging At 55° C.

| Sample ID | Viscosity @ 30 Days | VOC | Reactive Diluent | Scavenger | Solvent System | DIT 20 | DIT 40 | Gloss | Hardness (24 H) | Hardness (1 WK) |
|---|---|---|---|---|---|---|---|---|---|---|
| 64C | 3.7 | 1.63 | 746/TMPTA | Mole Sieve | Acetone | Pass | Slight Failure | 99.2 | 2 H | 4 H |
| 65C | 2.25 | 2.7 | 748 | Incosol | MIBK | Pass | Pass | 16.9 | H | B |
| 67C | 1.4 | 2.7 | 748 | Incosol | MPK | Pass | Pass | 15.3 | <B | B |
| 71C | 4.7 | 1.36 | 748 | Incosol | t-Butyl Acetate | Pass | Pass | 22.8 | <B | F |
| 73C | 0.65 | 1.41 | 748 | Incosol | Acetone | Pass | Pass | 36.9 | <B | <B |
| 74C | 3.7 | 1.62 | 748/TMPTA | Mole Sieve | Acetone | Pass | Pass | 91 | H | 4 H |
| 83C | 2.5 | 1.68 | 757 | Incosol | Acetone | Pass | Slight Failure | 49.6 | F | F |
| 84C | 5.5 | 1.63 | 757/TMPTA | Mole Sieve | Acetone | Pass | Pass | 95.1 | H | 4 H |
| 85C | 0.5 | 3.05 | None | Mole Sieve | MIBK/ Oxsol 100 | Pass | Very Slight Fail | 76.5 | H | 2 H |

The effect of different solvents was also evaluated. Table 11 shows the effect of various solvents using two different blocked amines: DETA blocked with MIBK, and xylylenediamine blocked with MIBK. The solvents from best to worst, regardless of reactive modifier or water scavenger, with respect to hindering gelation were: acetone, MPK, MIBK, t-butyl acetate, and p-chlorobenzotrifluoride. The inability of t-butyl acetate to hinder gelation could be due to the presence of 0.5–1.0% t-butyl alcohol, an impurity that could react with the epoxy resin.

A mixed solvent system comprised of equal parts p-chlorobenzotrifluoride/MIBK was evaluated (Sample 85C). The formulation showed no increase in viscosity after 30 day of accelerated aging. The calculated VOC level of the formulation was 3.05 lbs/gal, which is slightly higher than the target value of 2.8 lbs/gal. Other physical property values were good. Sample 85C displayed no viscosity increase although p-chlorobenzotrifluoride alone is the least effective solvent at retarding gelation.

Although not wishing to be bound by theory, we believe that these results are a function of the polarity and hydrogen bonding of the solvents. Table 12 shows a ranking of solvents and their polarity solubility parameters and hydrogen bonding solubility parameters. Oxygen containing solvent systems having both intermediate to high polarity (δP of 6–14) and high hydrogen bonding (δH of 9–14) are unacceptable for stable coating formulations. Systems with both low polarity (δP of 1–2) and low to intermediate hydrogen bonding capabilities (δH of 2–7) have poor capacity to stabilize a blocked amine epoxy coating precursor. Oxygenated solvents with intermediate polarity (δP of 5–10) and intermediate hydrogen bonding (δH of 4–7) are acceptable for stable single component epoxy coating precursors.

Thus, single component epoxy coating precursors made from blocked amines having an extended shelf life have been demonstrated. Coatings can made from these precursors having VOC levels of less than 3 lbs/gal.

Coating formulations made according to the present invention may contain additional components, including, but not limited to, pigments, such as titanium dioxide, fillers, such as silica, and other formulation aids, such as wetting agents, defoamers, flow aids, leveling agents, and the like.

TABLE 11

Effect of Solvent System on High Temperature Storage Stability and Solution Viscosity

| Ketimine + Epoxy Resin | Solvent | Stability at 55° C. (Viscosity) (Stokes) |
|---|---|---|
| DETA-MTBK | Toluene | None |
|  | MIBK | Sprayable after 15 days |
|  | 50/50 Toluene/MIBK | None |
| Xylylenediamine-MIBK | MIBK (a) | 19 after 30 days |
|  | MIBK (b) | 5.5 after 30 days |
|  | MPK (c) | 3.2 after 30 days |
|  | p-chlorobenzotrifluoride (d) | gelled after 30 days |
|  | 50/50 MIBK/p-chlorobenzotrifluoride (e) | 0.5 after 30 days |
|  | t-butyl acetate (f) | 13 after 30 days |
|  | acetone (g) | 0.85 after 30 days |

(a) contains mole sieves but no reactive diluent
(b) contains monofunctional reactive diluent (Epodil ™ 742) but no scavenger
(c) contains monofunctional reactive diluent (Epodil ™ 742) but no scavenger
(d) contains monofunctional reactive diluent (Epodil ™ 742) but no scavenger
(e) contains moles sieves but no reactive diluent
(f) contains Incosol-2 ™ and monofunctional reactive diluent (Epodil ™ 742)
(g) contains Incosol-2 ™ and monofunctional reactive diluent (Epodil ™ 742)

TABLE 12

Ranking of Solvents for Stability of Xylylenediamine-MIBK Epoxy Coatings

| Solvents | Ranking | Polarity (δP) | Hydrogen Bonding (δH) |
|---|---|---|---|
| Acetone | Good | 10.4 | 7 |
| MIBK | " | 6.1 | 4.1 |
| MPK | " | — | — |
| Ethyl Acetate | " | 5.3 | 7.2 |
| Dioxane | Poor | 1.8 | 7.4 |
| T-butyl acetate | " | — | — |
| Toluene | " | 1.4 | 2 |
| P-chlorobenzo trifluoride | Unacceptable | — | — |

TABLE 12-continued

Ranking of Solvents for Stability of Xylylenediamine-MIBK Epoxy Coatings

| Solvents | Ranking | Polarity (δP) | Hydrogen Bonding (δH) |
|---|---|---|---|
| Dimethylformamide | " | 13.7 | 11.3 |
| Benzyl Alcohol | " | 6.3 | 13.7 |

δP - Polar solubility parameter (MPa½)
δH - Hydrogen bonding solubility parameter (MPa½)

While certain representative embodiments and details have been shown for purposes of illustrating the invention, it will be apparent to those skilled in the art that various changes in the compositions and methods disclosed herein may be made without departing from the scope of the invention, which is defined in the appended claims.

What is claimed is:

1. A single component epoxy coating precursor comprising:
   an epoxy resin;
   a solvent; and
   a blocked amine;
   wherein the single component epoxy coating precursor has a viscosity after 30 days at a temperature of 55° C. of less than 16 stokes.

2. The single component epoxy coating precursor of claim 1 wherein the viscosity of the single component epoxy coating precursor after 30 days at a temperature of 55° C. is less than 13 stokes.

3. The single component epoxy coating precursor of claim 2 wherein the viscosity of the single component epoxy coating precursor after 30 days at a temperature of 55° C. is less than 7 stokes.

4. A single component epoxy coating precursor comprising:
   an epoxy resin;
   a reactive diluent;
   a solvent; and
   a blocked amine;
   wherein the single component epoxy coating precursor has a viscosity after 30 days at a temperature of 55° C. of less than 16 stokes.

5. The single component epoxy coating precursor of claim 4 wherein the reactive diluent is selected from modified glycidyl ethers, acrylates, methacrylates, urethane acrylates and combinations thereof.

6. The single component epoxy coating precursor of claim 4 wherein the reactive diluent comprises a modified glycidyl ether.

7. The single component epoxy coating precursor of claim 1 further comprising a water scavenger.

8. The single component epoxy coating precursor of claim 7 wherein the water scavenger is selected from molecular sieves, monocyclic bifunctional oxazolidines and combinations thereof.

9. The single component epoxy coating precursor of claim 1 further comprising a pigment.

10. The single component epoxy coating precursor of claim 9 wherein the pigment is selected from titanium dioxide, diarylide yellow, iron oxide, raw umber, burnt umber, phthalocyanine blue, cobalt blue, chinese blue, phthalocyanine green, toluidine red, quinacridone red, dicerylide orange, carbon black, furnale black, lampblack, leafing aluminum and non-leaving aluminum.

11. The single component epoxy coating precursor of claim 1 wherein the solvent is selected from acetone, p-chlorobenzotrifluoride, t-butyl acetate, methyl isobutyl ketone, methyl propyl ketone and combinations thereof.

12. The single component epoxy coating precursor of claim 1 wherein the epoxy resin is selected from aliphatic epoxy resins, cycloaliphatic epoxy resins, aromatic epoxy resins and combinations thereof.

13. The single component epoxy coating precursor of claim 1 wherein the epoxy resin comprises a difunctional bisphenol A/epichlorohydrin derived epoxy resin.

14. A single component epoxy coating precursor comprising:
   an epoxy resin;
   a solvent; and
   a blocked amine;
   wherein the single component epoxy coating precursor has a viscosity after 30 days at a temperature of 55° C. of less than 16 stokes and wherein the single component epoxy coating precursor has a VOC level of less than about 3 lbs/gal.

15. The single component epoxy coating precursor of claim 14 wherein the single component epoxy coating precursor has a VOC level of less than about 2.8 lbs/gal.

16. The single component epoxy coating precursor of claim 1 wherein the blocked amine comprises a ketone-based blocked amine.

17. The single component epoxy coating precursor of claim 16 wherein the ketone-based blocked amine comprises an amine blocked with a ketone having a molecular weight in the range of about 30 to about 600.

18. The single component epoxy coating precursor of claim 16 wherein the ketone-based blocked amine comprises an amine blocked with a ketone containing between about 3 and 14 carbon atoms.

19. The single component epoxy coating precursor of claim 1 wherein the blocked amine comprises an aldehyde-based blocked amine.

20. The single component epoxy coating precursor of claim 19 wherein the aldehyde-based blocked amine comprises an amine blocked with an aldehyde having a molecular weight in the range of about 30 to about 600.

21. The single component epoxy coating precursor of claim 19 wherein the aldehyde-based blocked amine comprises an amine blocked with an aldehyde containing between about 2 and 14 carbon atoms.

22. The single component epoxy coating precursor of claim 1 wherein the blocked amine comprises a methyl isobutyl ketone-xylylenediamine based blocked amine.

23. A method for making a single component epoxy coating precursor comprising:
   drying an epoxy resin and a blocked amine;
   combining and mixing the epoxy resin, the blocked amine, and a solvent to form the single component epoxy coating precursor, wherein the single component epoxy coating precursor has a viscosity after 30 days at a temperature of 55° C. of less than 16 stokes.

24. The method of claim 23 wherein the viscosity of the single component epoxy coating precursor after 30 days at a temperature of 55° C. is less than 13 stokes.

25. The method of claim 23 wherein the viscosity of the single component epoxy coating precursor after 30 days at a temperature of 55° C. is less than 7 stokes.

26. A method for making a single component epoxy coating precursor comprising:

drying an epoxy resin and a blocked amine;

combining and mixing the epoxy resin, the blocked amine, a reactive diluent, and a solvent to form the single component epoxy coating precursor, wherein the single component epoxy coating precursor has a viscosity after 30 days at a temperature of 55° C. of less than 16 stokes.

27. The method of claim 26 wherein the reactive diluent is selected from modified glycidyl ethers, acrylates, methacrylates, urethane acrylates and combinations thereof.

28. The method of claim 26 wherein the reactive diluent comprises a modified glycidyl ether.

29. The method of claim 23 further comprising adding a water scavenger.

30. The method of claim 29 wherein the water scavenger is selected from molecular sieves, monocyclic bifunctional oxazolidines and combinations thereof.

31. The method of claim 23 wherein the solvent is selected from acetone, p-chlorobenzotrifluoride, t-butyl acetate, methyl isobutyl ketone, methyl propyl ketone and combinations thereof.

32. The method of claim 23 wherein the epoxy resin is selected from aliphatic epoxy resins, cycloaliphatic epoxy resins, aromatic epoxy resins and combinations thereof.

33. The method of claim 23 wherein the epoxy resin comprises a difunctional bisphenol A/epichlorohydrin derived epoxy resin.

34. A method for making a single component epoxy coating precursor comprising:

drying an epoxy resin and a blocked amine;

combining and mixing the epoxy resin, the blocked amine, and a solvent to form the single component epoxy coating precursor, wherein the single component epoxy coating precursor has a viscosity after 30 days at a temperature of 55° C. of less than 16 stokes and wherein the single component epoxy coating precursor has a VOC level of less than about 3 lbs/gal.

35. The method of claim 23 wherein the single component epoxy coating precursor has a VOC level of less than about 2.8 lbs/gal.

36. The method of claim 23 wherein the blocked amine comprises a ketone-based blocked amine.

37. The method of claim 36 wherein the ketone-based blocked amine comprises an amine blocked with a ketone having a molecular weight in the range of about 30 to about 600.

38. The method of claim 36 wherein the ketone-based blocked amine comprises an amine blocked with a ketone containing between about 3 and 14 carbon atoms.

39. The method of claim 23 wherein the blocked amine comprises an aldehyde-based blocked amine.

40. The method of claim 39 wherein the aldehyde-based blocked amine comprises an amine blocked with an aldehyde having a molecular weight in the range of about 30 to about 600.

41. The method of claim 39 wherein the aldehyde-based blocked amine comprises an amine blocked with an aldehyde containing between about 2 and 14 carbon atoms.

42. The method of claim 23 wherein the blocked amine comprises a methyl isobutyl ketone-xylylenediamine based blocked amine.

43. The method of claim 23 further comprising adding a pigment.

44. The method of claim 43 wherein the pigment is selected from titanium dioxide, diarylide yellow, iron oxide, raw umber, burnt umber, phthalocyanine blue, cobalt blue, chinese blue, phthalocyanine green, toluidine red, quinacridone red, dicerylide orange, carbon black, furnale black, lampblack, leafing aluminum and non-leaving aluminum.

45. The method of claim 23 wherein the blocked amine is made by a process comprising:

mixing a solvent capable of forming an azeotrope with water, an amine, and an amine blocker selected from ketones and aldehydes in a reaction vessel to form a reaction mixture;

removing ambient moisture from the reaction vessel;

reacting the amine and the amine blocker to form the blocked amine and water of reaction;

removing the water of reaction from the reaction mixture while the amine and the amine blocker are reacted; and recovering the blocked amine while maintaining the absence of moisture.

46. The method of claim 45 wherein the solvent capable of forming an azeotrope with water is capable of forming a binary or ternary azeotrope with water.

47. The method of claim 45 wherein the solvent capable of forming an azeotrope with water is selected from toluene, xylene and combinations thereof.

48. The method of claim 45 wherein the solvent capable of forming an azeotrope with water comprises toluene.

49. The method of claim 45 wherein the amine comprises a polyamine.

50. The method of claim 45 wherein the amine is selected from diethylenetriamine, m-xylylenediamine and combinations thereof.

51. The method of claim 45 wherein the amine comprises m-xylylenediamine.

52. The method of claim 45 wherein the amine blocker is a ketone.

53. The method of claim 52 wherein the ketone has a molecular weight in the range of about 30 to about 600.

54. The method of claim 52 wherein the ketone contains between about 3 and 14 carbon atoms.

55. The method of claim 52 wherein the ketone is selected from methyl isobutyl ketone, methyl ethyl ketone, acetone, phorone, heptanedione, tetramethylheptanedione, adamantone, acetonyl acetone, methylpropylketone and combinations thereof.

56. The method of claim 52 wherein the ketone comprises methyl isobutyl ketone.

57. The method of claim 45 wherein the amine blocker is an aldehyde.

58. The method of claim 57 wherein the aldehyde has a molecular weight in the range of about 30 to about 600.

59. The method of claim 57 wherein the aldehyde contains between about 2 and 14 carbon atoms.

60. The method of claim 57 wherein the aldehyde is selected from benzaldehyde, salicylaldehyde and combinations thereof.

61. The method of claim 57 wherein the aldehyde comprises benzaldehyde.

62. The method of claim 45 wherein the solvent capable of forming an azeotrope with water comprises toluene, the amine comprises m-xylylenediamine, and the amine blocker comprises methyl isobutyl ketone.

63. The single component epoxy resin precursor of claim 1 wherein the solvent has an intermediate polar solubility parameter and an intermediate hydrogen bonding solubility parameter.

64. The method of claim 23 wherein the solvent has an intermediate polar solubility parameter and an intermediate hydrogen bonding solubility parameter.

65. The single component epoxy resin precursor of claim 1 with the proviso that the blocked amine is not the reaction product of one or more compounds containing at least one epoxy group and one or more imines having at least one amino hydrogen.

66. The single component epoxy resin precursor of claim 1 with the proviso that the blocked amine is not a heterocycle-containing compound having a backbone chain selected from the group consisting of polyether, polyvinyl, polyester, polyamide, polycarbonate, and novalac chains and at least two heterocyclic groups of the following general formula as side chains,

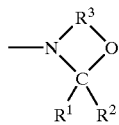

wherein $R^1$ and $R^2$ may be the same or different and each represents hydrogen, straight chain or branched $C_1$ to $C_6$ alkyl or alkenyl, or $C_6$ to $C_8$ aryl; or $R^1$ and $R^2$ taken together with the adjacent carbon atom, represents $C_5$ to $C_7$ cycloalkyl: $R^3$ represents $C_1$ to $C_{10}$ alkylene.

67. The method of claim 23 with the proviso that the blocked amine is not the reaction product of one or more compounds containing at least one epoxy group and one or more imines having at least one amino hydrogen.

68. The method of claim 23 with the proviso that the blocked amine is not a heterocycle-containing compound having a backbone chain selected from the group consisting of polyether, polyvinyl, polyester, polyamide, polycarbonate, and novalac chains and at least two heterocyclic groups of the following general formula as side chains,

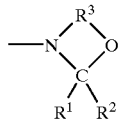

wherein $R^1$ and $R^2$ may be the same or different and each represents hydrogen, straight chain or branched $C_1$ to $C_6$ alkyl or alkenyl, or $C_6$ to $C_8$ aryl; or $R^1$ and $R^2$ taken together with the adjacent carbon atom, represents $C_5$ to $C_7$ cycloalkyl: $R^3$ represents $C_1$ to $C_{10}$ alkylene.

69. The single component epoxy coating precursor of claim 4 wherein the viscosity of the single component epoxy coating precursor after 30 days at a temperature of 55° C. is less than 13 stokes.

70. The single component epoxy coating precursor of claim 4 wherein the viscosity of the single component epoxy coating precursor after 30 days at a temperature of 55° C. is less than 7 stokes.

71. The single component epoxy coating precursor of claim 4 further comprising a water scavenger.

72. The single component epoxy coating precursor of claim 71 wherein the water scavenger is selected from molecular sieves, monocyclic bifunctional oxazolidines and combinations thereof.

73. The single component epoxy coating precursor of claim 4 further comprising a pigment.

74. The single component epoxy coating precursor of claim 73 wherein the pigment is selected from titanium dioxide, diarylide yellow, iron oxide, raw umber, burnt umber, phthalocyanine blue, cobalt blue, chinese blue, phthalocyanine green, toluidine red, quinacridone red, dicerylide orange, carbon black, furnale black, lampblack, leafing aluminum and non-leaving aluminum.

75. The single component epoxy coating precursor of claim 4 wherein the solvent is selected from acetone, p-chlorobenzotrifluoride, t-butyl acetate, methyl isobutyl ketone, methyl propyl ketone and combinations thereof.

76. The single component epoxy coating precursor of claim 4 wherein the epoxy resin is selected from aliphatic epoxy resins, cycloaliphatic epoxy resins, aromatic epoxy resins and combinations thereof.

77. The single component epoxy coating precursor of claim 4 wherein the epoxy resin comprises a difunctional bisphenol A/epichlorohydrin derived epoxy resin.

78. The single component epoxy coating precursor of claim 4 wherein the single component epoxy coating precursor has a VOC level of less than about 3 lbs/gal.

79. The single component epoxy coating precursor of claim 78 wherein the single component epoxy coating precursor has a VOC level of less than about 2.8 lbs/gal.

80. The single component epoxy coating precursor of claim 4 wherein the blocked amine comprises a ketone-based blocked amine.

81. The single component epoxy coating precursor of claim 80 wherein the ketone-based blocked amine comprises an amine blocked with a ketone having a molecular weight in the range of about 30 to about 600.

82. The single component epoxy coating precursor of claim 80 wherein the ketone-based blocked amine comprises an amine blocked with a ketone containing between about 3 and 14 carbon atoms.

83. The single component epoxy coating precursor of claim 4 wherein the blocked amine comprises an aldehyde-based blocked amine.

84. The single component epoxy coating precursor of claim 83 wherein the aldehyde-based blocked amine comprises an amine blocked with an aldehyde having a molecular weight in the range of about 30 to about 600.

85. The single component epoxy coating precursor of claim 83 wherein the aldehyde-based blocked amine comprises an amine blocked with an aldehyde containing between about 2 and 14 carbon atoms.

86. The single component epoxy coating precursor of claim 4 wherein the blocked amine comprises a methyl isobutyl ketone-xylylenediamine based blocked amine.

87. The method of claim 26 wherein the viscosity of the single component epoxy coating precursor after 30 days at a temperature of 55° C. is less than 13 stokes.

88. The method of claim 26 wherein the viscosity of the single component epoxy coating precursor after 30 days at a temperature of 55° C. is less than 7 stokes.

89. The method of claim 26 wherein the reactive diluent is selected from modified glycidyl ethers, acrylates, methacrylates, urethane acrylates and combinations thereof.

90. The method of claim 26 wherein the reactive diluent comprises a modified glycidyl ether.

91. The method of claim 26 further comprising adding a water scavenger.

92. The method of claim 91 wherein the water scavenger is selected from molecular sieves, monocyclic bifunctional oxazolidines and combinations thereof.

93. The method of claim 26 wherein the solvent is selected from acetone, p-chlorobenzotrifluoride, t-butyl acetate, methyl isobutyl ketone, methyl propyl ketone and combinations thereof.

94. The method of claim 26 wherein the epoxy resin is selected from aliphatic epoxy resins, cycloaliphatic epoxy resins, aromatic epoxy resins and combinations thereof.

95. The method of claim 26 wherein the epoxy resin comprises a difunctional bisphenol A/epichlorohydrin derived epoxy resin.

96. The method of claim 26 wherein the single component epoxy coating precursor has a VOC level of less than about 3 lbs/gal.

97. The method of claim 26 wherein the single component epoxy coating precursor has a VOC level of less than about 2.8 lbs/gal.

98. The method of claim 26 wherein the blocked amine comprises a ketone-based blocked amine.

99. The method of claim 98 wherein the ketone-based blocked amine comprises an amine blocked with a ketone having a molecular weight in the range of about 30 to about 600.

100. The method of claim 98 wherein the ketone-based blocked amine comprises an amine blocked with a ketone containing between about 3 and 14 carbon atoms.

101. The method of claim 26 wherein the blocked amine comprises an aldehyde-based blocked amine.

102. The method of claim 101 wherein the aldehyde-based blocked amine comprises an amine blocked with an aldehyde having a molecular weight in the range of about 30 to about 600.

103. The method of claim 101 wherein the aldehyde-based blocked amine comprises an amine blocked with an aldehyde containing between about 2 and 14 carbon atoms.

104. The method of claim 26 wherein the blocked amine comprises a methyl isobutyl ketone-xylylenediamine based blocked amine.

105. The method of claim 26 further comprising adding a pigment.

106. The method of claim 105 wherein the pigment is selected from titanium dioxide, diarylide yellow, iron oxide, raw umber, burnt umber, phthalocyanine blue, cobalt blue, chinese blue, phthalocyanine green, toluidine red, quinacridone red, dicerylide orange, carbon black, furnale black, lampblack, leafing aluminum and non-leaving aluminum.

107. The method of claim 26 wherein the blocked amine is made by a process comprising:
mixing a solvent capable of forming an azeotrope with water, an amine, and an amine blocker selected from ketones and aldehydes in a reaction vessel to form a reaction mixture;
removing ambient moisture from the reaction vessel;
reacting the amine and the amine blocker to form the blocked amine and water of reaction;
removing the water of reaction from the reaction mixture while the amine and the amine blocker are reacted; and
recovering the blocked amine while maintaining the absence of moisture.

108. The method of claim 107 wherein the solvent capable of forming an azeotrope with water is capable of forming a binary or ternary azeotrope with water.

109. The method of claim 107 wherein the solvent capable of forming an azeotrope with water is selected from toluene, xylene and combinations thereof.

110. The method of claim 107 wherein the solvent capable of forming an azeotrope with water comprises toluene.

111. The method of claim 107 wherein the amine comprises a polyamine.

112. The method of claim 107 wherein the amine is selected from diethylenetriamine, m-xylylenediamine and combinations thereof.

113. The method of claim 107 wherein the amine comprises m-xylylenediamine.

114. The method of claim 107 wherein the amine blocker is a ketone.

115. The method of claim 114 wherein the ketone has a molecular weight in the range of about 30 to about 600.

116. The method of claim 114 wherein the ketone contains between about 3 and 14 carbon atoms.

117. The method of claim 114 wherein the ketone is selected from methyl isobutyl ketone, methyl ethyl ketone, acetone, phorone, heptanedione, tetramethylheptanedione, adamantone, acetonyl acetone, methylpropylketone and combinations thereof.

118. The method of claim 114 wherein the ketone comprises methyl isobutyl ketone.

119. The method of claim 107 wherein the amine blocker is an aldehyde.

120. The method of claim 119 wherein the aldehyde has a molecular weight in the range of about 30 to about 600.

121. The method of claim 119 wherein the aldehyde contains between about 2 and 14 carbon atoms.

122. The method of claim 119 wherein the aldehyde is selected from benzaldehyde, salicylaldehyde and combinations thereof.

123. The method of claim 119 wherein the aldehyde comprises benzaldehyde.

124. The method of claim 107 wherein the solvent capable of forming an azeotrope with water comprises toluene, the amine comprises m-xylylenediamine, and the amine blocker comprises methyl isobutyl ketone.

125. The method of claim 26 wherein the solvent has an intermediate polar solubility parameter and an intermediate hydrogen bonding solubility parameter.

126. The single component epoxy resin precursor of claim 4 wherein the solvent has an intermediate polar solubility parameter and an intermediate hydrogen bonding solubility parameter.

127. The single component epoxy coating precursor of claim 14 wherein the single component epoxy coating precursor has a VOC level of less than about 2.8 lbs/gal.

128. The single component epoxy coating precursor of claim 1 further comprising a reactive diluent.

129. The single component epoxy coating precursor of claim 14 further comprising a water scavenger.

130. The single component epoxy coating precursor of claim 14 further comprising a pigment.

131. The single component epoxy coating precursor of claim 14 wherein the solvent is selected from acetone, p-chlorobenzotrifluoride, t-butyl acetate, methyl isobutyl ketone, methyl propyl ketone and combinations thereof.

132. The single component epoxy coating precursor of claim 14 wherein the epoxy resin is selected from aliphatic epoxy resins, cycloaliphatic epoxy resins, aromatic epoxy resins and combinations thereof.

133. The single component epoxy coating precursor of claim 14 wherein the blocked amine comprises a methyl isobutyl ketone-xylylenediamine based blocked amine.

134. The single component epoxy resin precursor of claim 14 wherein the solvent has an intermediate polar solubility parameter and an intermediate hydrogen bonding solubility parameter.

135. The single component epoxy resin precursor of claim 14 wherein the blocked amine is an amine blocked with a ketone selected from methyl isobutyl ketone, methyl ethyl ketone, acetone, phorone, heptanedione, tetramethylheptanedione, adamantone, acetonyl acetone, methylpropylketone and combinations thereof.

136. The single component epoxy resin precursor of claim 14 wherein the blocked amine is an amine blocked with an aldehyde is selected from benzaldehyde, salicylaldehyde and combinations thereof.

137. A method for making a single component epoxy coating precursor comprising:

drying an epoxy resin and a blocked amine;

combining and mixing the epoxy resin, the blocked amine, and a solvent to form the single component epoxy coating precursor, wherein the single component epoxy coating precursor has a viscosity after 30 days at a temperature of 55° C. of less than 16 stokes and wherein the single component epoxy coating precursor has a VOC level of less than about 3 lbs/gal.

138. The method of claim 137 wherein the single component epoxy coating precursor has a VOC level of less than about 2.8 lbs/gal.

139. The method of claim 137 further comprising adding a reactive diluent.

140. The method of claim 137 further comprising adding a water scavenger.

141. The method of claim 137 wherein the solvent is selected from acetone, p-chlorobenzotrifluoride, t-butyl acetate, methyl isobutyl ketone, methyl propyl ketone and combinations thereof.

142. The method of claim 137 wherein the epoxy resin is selected from aliphatic epoxy resins, cycloaliphatic epoxy resins, aromatic epoxy resins and combinations thereof.

143. The method of claim 137 further comprising adding a pigment.

144. The method of claim 137 wherein the viscosity of the single component epoxy coating precursor after 30 days at a temperature of 55° C. is less than 13 stokes.

145. The method of claim 137 wherein the viscosity of the single component epoxy coating precursor after 30 days at a temperature of 55° C. is less than 7 stokes.

146. The method of claim 137 wherein the solvent is selected from acetone, p-chlorobenzotrifluoride, t-butyl acetate, methyl isobutyl ketone, methyl propyl ketone and combinations thereof.

147. The method of claim 137 wherein the epoxy resin is selected from aliphatic epoxy resins, cycloaliphatic epoxy resins, aromatic epoxy resins and combinations thereof.

148. The method of claim 137 wherein the blocked amine is made by a process comprising:

mixing a solvent capable of forming an azeotrope with water, an amine, and an amine blocker selected from ketones and aldehydes in a reaction vessel to form a reaction mixture;

removing ambient moisture from the reaction vessel;

reacting the amine and the amine blocker to form the blocked amine and water of reaction;

removing the water of reaction from the reaction mixture while the amine and the amine blocker are reacted; and recovering the blocked amine while maintaining the absence of moisture.

149. The method of claim 148 wherein the solvent capable of forming an azeotrope with water is capable of forming a binary or ternary azeotrope with water.

150. The method of claim 148 wherein the solvent capable of forming an azeotrope with water is selected from toluene, xylene and combinations thereof.

151. The method of claim 148 wherein the solvent capable of forming an azeotrope with water comprises toluene, the amine comprises m-xylylenediamine, and the amine blocker comprises methyl isobutyl ketone.

152. The method of claim 148 wherein amine blocker is a ketone is selected from methyl isobutyl ketone, methyl ethyl ketone, acetone, phorone, heptanedione, tetramethylheptanedione, adamantone, acetonyl acetone, methylpropylketone and combinations thereof.

153. The method of claim 148 wherein the amine blocker is an aldehyde is selected from benzaldehyde, salicylaldehyde and combinations thereof.

154. The method of claim 148 wherein the solvent has an intermediate polar solubility parameter and an intermediate hydrogen bonding solubility parameter.

* * * * *

UNITED STATES PATENT AND TRADEMARK OFFICE
CERTIFICATE OF CORRECTION

PATENT NO. : 6,649,673 B2
DATED : November 18, 2003
INVENTOR(S) : Browning et al.

It is certified that error appears in the above-identified patent and that said Letters Patent is hereby corrected as shown below:

<u>Title page,</u>
Item [75], Inventors, "Bhima Rao Vajayendran" should be
-- Bhima Rao Vijayendran --

<u>Column 15,</u>
Table 2, under "MEK (Dbl. Rubs)", "100 (no effect" should be -- 100 (no effect) --

<u>Column 27,</u>
Table 8, 35C, "Classic "high h-low" loss attern of incompatibility" should be
-- Classic "high-low" gloss pattern of incompatibility --

<u>Column 31,</u>
Table 10, DIT 40, 47C, "Pass Slight Fail" should be -- Pass --

<u>Column 34,</u>
Line 31, Table 11, "DETA-MTBK" should be -- DETA-MIBK --

Signed and Sealed this

Eighteenth Day of May, 2004

JON W. DUDAS
*Acting Director of the United States Patent and Trademark Office*